United States Patent
Kogo

(10) Patent No.: US 12,207,928 B2
(45) Date of Patent: *Jan. 28, 2025

(54) AROUSAL LEVEL CONTROL APPARATUS, AROUSAL LEVEL CONTROL METHOD, AND RECORDING MEDIUM

(71) Applicant: NEC Corporation, Tokyo (JP)

(72) Inventor: Takuma Kogo, Tokyo (JP)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,506

(22) Filed: Oct. 31, 2023

(65) Prior Publication Data

US 2024/0057915 A1 Feb. 22, 2024

Related U.S. Application Data

(63) Continuation of application No. 17/427,234, filed as application No. PCT/JP2020/003701 on Jan. 31, 2020, now Pat. No. 11,826,147.

(30) Foreign Application Priority Data

Feb. 4, 2019 (JP) .................................. 2019-018212

(51) Int. Cl.
*A61B 5/18* (2006.01)
*A61M 21/00* (2006.01)

(52) U.S. Cl.
CPC .............. *A61B 5/18* (2013.01); *A61M 21/00* (2013.01); *A61M 2021/0083* (2013.01)

(58) Field of Classification Search
CPC .......... G08B 21/02; G08B 21/06; A61B 5/18; A61B 5/746

See application file for complete search history.

(56) References Cited

U.S. PATENT DOCUMENTS 11,273,778 B1 * 3/2022 Lakhani .............. B60R 16/0373
2017/0020432 A1 1/2017 Kusukame .............. G06F 3/165
(Continued)

FOREIGN PATENT DOCUMENTS

CN 110268451 A 9/2019 .......... A61B 5/0205
JP H09140799 A 6/1997
(Continued)

OTHER PUBLICATIONS

International Search Report for PCT Application No. PCT/JP2020/003701, mailed on Mar. 24, 2020.
(Continued)

*Primary Examiner* — Kevin Kim
(74) *Attorney, Agent, or Firm* — Sughrue Mion, PLLC

(57) ABSTRACT

An arousal level control apparatus calculates a setting value of a control device under a constraint condition using an arousal level optimization model so that a value of an objective function is maximized. The control device affects a physical quantity of a surrounding environment that affects arousal level of a subject. The arousal level optimization model includes the constraint condition and the objective function. The constraint condition includes a physical quantity prediction model, an arousal level prediction model, and a setting value range condition that the setting value is within a predetermined range. The physical quantity prediction model is an explicit function that includes the physical quantity and the setting value as explanatory variables and has a predicted value of the physical quantity as an explained variable.

7 Claims, 12 Drawing Sheets

(56) References Cited

U.S. PATENT DOCUMENTS

| | | | |
|---|---|---|---|
| 2017/0119297 A1 | 5/2017 | Flax et al. | |
| 2018/0110958 A1 | 4/2018 | Wu et al. | |
| 2019/0380637 A1 | 12/2019 | Komoda | |
| 2020/0240670 A1 | 7/2020 | Kitagawa et al. | |
| 2021/0097370 A1 | 4/2021 | Agnihotram | |

FOREIGN PATENT DOCUMENTS

| | | | |
|---|---|---|---|
| JP | 2006349288 A | 12/2006 | |
| JP | 2013012029 A | 1/2013 | |
| JP | 2013027570 A | 2/2013 | |
| JP | 6043933 B2 | 12/2016 | |
| JP | 2017148604 A | 8/2017 | |
| JP | 2018025870 A | 2/2018 | |
| JP | 2018066555 A | 4/2018 | |
| JP | 2018088966 A | 6/2018 | |
| JP | 2018134274 A | 8/2018 | |
| JP | 2018524137 A | 8/2018 | |
| JP | 6387173 B1 | 9/2018 | |
| WO | WO-2019017124 A1 | 1/2019 | ............. A61B 5/162 |

OTHER PUBLICATIONS

US Office Action for U.S. Appl. No. 18/385,606, mailed on Jun. 5, 2024.

\* cited by examiner

AROUSAL LEVEL CONTROL APPARATUS, AROUSAL LEVEL CONTROL METHOD, AND RECORDING MEDIUM

This application is a Continuation of U.S. application Ser. No. 17/427,234 filed on Jul. 30, 2021, which is a National Stage Entry of PCT/JP2020/003701 filed on Jan. 31, 2020, which claims priority from Japanese Patent Application 2019-018212 filed on Feb. 4, 2019, the contents of all of which are incorporated herein by reference, in their entirety.

TECHNICAL FIELD

The present invention relates to an arousal level control apparatus, an arousal level control method, and a recording medium.

BACKGROUND ART

There has been proposed a technique in which a user's physiological information is acquired and the user's arousal level is calculated from the acquired physiological information (for example, Patent Documents 1, 2). Here, the arousal level is an index indicating the degree of awakeness. The lower the value of the arousal level, the drowsier the subject is.

In the state where the level of arousal is low, the work efficiency often decreases when the user performs a task. Therefore, the state where the arousal level is low is not an appropriate state for performing a task. For example, in office work, work efficiency decreases, and in driving a car, distracted driving increases. Thus, the state where the level of arousal is low tends to be an undesired state for various tasks.

Therefore, there have been proposed systems for controlling the environment of the user so that the level of arousal is improved or brought into an appropriate range (Patent Documents 3, 4, and 5).

Patent Document 3 discloses a system for controlling the level of arousal for a vehicle driver in which settings of environment control devices for air conditioning, lighting, and so forth are changed to predetermined settings, when a predicted value of the level of arousal of the user in the case where the state of current environmental state continues, falls below a predetermined threshold value.

Patent Document 4 discloses a system for controlling the level of arousal for a vehicle driver in which the combination of devices that stimulate the five senses such as air conditioning and lighting and the intensities are determined and controlled on the basis of predetermined settings, according to where the user's current state is, in particular, how far away from the desired range the user's current state is in a two-axis coordinate system consisting of an evaluation axis representing drowsy-arousal level and an evaluation axis representing comfort-discomfort.

Patent Document 5 discloses a system for controlling the level of arousal for a vehicle driver in which warm/cold stimuli caused by changes in temperature are given to the user by periodically switching the air conditioning device between predetermined operating modes (temperature, air volume setting), when the level of arousal of the subject falls below a preset threshold value.

Moreover, there is a technique for acquiring and processing user information or information on their surrounding environment.

For example, the mood estimation system disclosed in Patent Document 6 is such that the mood of a subject is indexed based only on the heart rate of the subject, and if the index value deviates from a preliminarily set range, the mood of the subject is represented as an index value on the basis of the subject's multiple physiological information, and multiple environmental information of the subject's surrounding environment.

Also, the air conditioning management system disclosed in Patent Document 7 calculates a predicted environmental value after a predetermined amount of time has elapsed on the basis of the environmental value detected by a detection device, and parameters of an air conditioning device are calculated on the basis of the environmental value and the predicted environmental value and are transmitted to the air conditioning device.

Moreover, in the method for maintaining arousal level disclosed in Patent Document 8, the level of arousal is detected from the deep body temperature of the worker such as tympanic temperature, and when the level of the worker's arousal appears to be decreasing, the wakening effect of light stimulation is given to the worker by changing the illuminance from an illuminance suitable for work to an even higher illuminance.

Furthermore, the drowsiness estimation device disclosed in Patent Document 9 includes a neural network having a structure with two layers, namely, an image processing neural network and a drowsiness estimation neural network. The image processing neural network estimates the age and gender of the user and also extracts specific behaviors and states of the user that indicate a state of drowsiness, such as closed eyes. The drowsiness estimation neural network obtains the drowsiness state of the user based on the result of extracting the specific behavior and the state of the user that indicate a state of drowsiness and on the detection result of an indoor environment information sensor while also taking the age and gender of the user into consideration.

Patent Document 9 discloses that the control unit of the air conditioning device calculates air-conditioning control content so that the estimated drowsiness level is equal to or less than a threshold value, and executes the calculated air-conditioning control. Furthermore, Patent Document 9 discloses that if the desired change is not observed in the user's behavior and state, the estimated behavior in the drowsy state is potentially departing from that in the actual drowsy state, and therefore the estimation model is updated.

PRIOR ART DOCUMENTS

Patent Documents

[Patent Document 1] Japanese Patent No. 6043933
[Patent Document 2] Japanese Unexamined Patent Application, First Publication No. 2018-134274
[Patent Document 3] Japanese Unexamined Patent Application, First Publication No. 2017-148604
[Patent Document 4] Japanese Unexamined Patent Application, First Publication No. 2018-025870
[Patent Document 5] Japanese Unexamined Patent Application, First Publication No. 2013-012029
[Patent Document 6] Japanese Unexamined Patent Application, First Publication No. 2018-088966
[Patent Document 7] Japanese Unexamined Patent Application, First Publication No. 2006-349288
[Patent Document 8] Japanese Unexamined Patent Application, First Publication No. H9-140799
[Patent Document 9] Japanese Patent No. 6387173

SUMMARY OF THE INVENTION

Problem to be Solved by the Invention

When a device or a system works on the environment surrounding an arousal level control subject to perform the arousal level control, it is appropriate that the device or the system can more accurately presume the effect of its work on the surrounding environment on the arousal level in order to perform the arousal level control with high accuracy.

An example object of the present invention is to provide an arousal level control apparatus, an arousal level control method, and a recording medium capable of solving the problems mentioned above.

Means for Solving the Problem

According to a first example aspect of the present invention, an arousal level control apparatus includes:

a setting value calculation means for calculating a setting value of a control device under a constraint condition using an arousal level optimization model so that a value of an objective function is maximized, the control device affecting a physical quantity of a surrounding environment that affects arousal level of a subject, the arousal level optimization model including the constraint condition and the objective function, the constraint condition including a physical quantity prediction model, an arousal level prediction model, and a setting value range condition that the setting value is within a predetermined range, the physical quantity prediction model being an explicit function that includes the physical quantity and the setting value as explanatory variables and has a predicted value of the physical quantity as an explained variable, the arousal level prediction model being an explicit function that includes the physical quantity and variation thereof over time as explanatory variables and has a predicted value of variation of the arousal level over time as an explained variable, the objective function expressing a total value or an average value of a predicted value for one or more targets including the target, the predicted value for the one or more targets being a predicted value of variation in the arousal level for the one or more subjects and two or more time steps that satisfies a predetermined condition; and a setting means for setting the calculated setting value to the control device.

According to a second example aspect of the present invention, an arousal level control method executed by a computer, includes:

calculating a setting value of a control device under a constraint condition using an arousal level optimization model so that a value of an objective function is maximized, the control device affecting a physical quantity of a surrounding environment that affects arousal level of a subject, the arousal level optimization model including the constraint condition and the objective function, the constraint condition including a physical quantity prediction model, an arousal level prediction model, and a setting value range condition that the setting value is within a predetermined range, the physical quantity prediction model being an explicit function that includes the physical quantity and the setting value as explanatory variables and has a predicted value of the physical quantity as an explained variable, the arousal level prediction model being an explicit function that includes the physical quantity and variation thereof over time as explanatory variables and has a predicted value of variation of the arousal level over time as an explained variable, the objective function expressing a total value or an average value of a predicted value for one or more targets including the target, the predicted value for the one or more targets being a predicted value of variation in the arousal level for the one or more subjects and two or more time steps that satisfies a predetermined condition; and setting the calculated setting value to the control device.

According to a third example aspect of the present invention, a recording medium stores a program causing a computer to execute:

calculating a setting value of a control device under a constraint condition using an arousal level optimization model so that a value of an objective function is maximized, the control device affecting a physical quantity of a surrounding environment that affects arousal level of a subject, the arousal level optimization model including the constraint condition and the objective function, the constraint condition including a physical quantity prediction model, an arousal level prediction model, and a setting value range condition that the setting value is within a predetermined range, the physical quantity prediction model being an explicit function that includes the physical quantity and the setting value as explanatory variables and has a predicted value of the physical quantity as an explained variable, the arousal level prediction model being an explicit function that includes the physical quantity and variation thereof over time as explanatory variables and has a predicted value of variation of the arousal level over time as an explained variable, the objective function expressing a total value or an average value of a predicted value for one or more targets including the target, the predicted value for the one or more targets being a predicted value of variation in the arousal level for the one or more subjects and two or more time steps that satisfies a predetermined condition; and setting the calculated setting value to the control device.

Effect of the Invention

According to an example embodiment of the present invention, when performing arousal level control, it is possible to more accurately grasp the influence of the action on the surrounding environment on arousal level.

EXAMPLE EMBODIMENT

Hereinafter, example embodiments of the present invention are described; however, the present invention within the scope of the claims is not limited by the following example embodiments. Furthermore, all the combinations of features described in the example embodiment may not be essential for the solving means of the invention.

Figure 1:
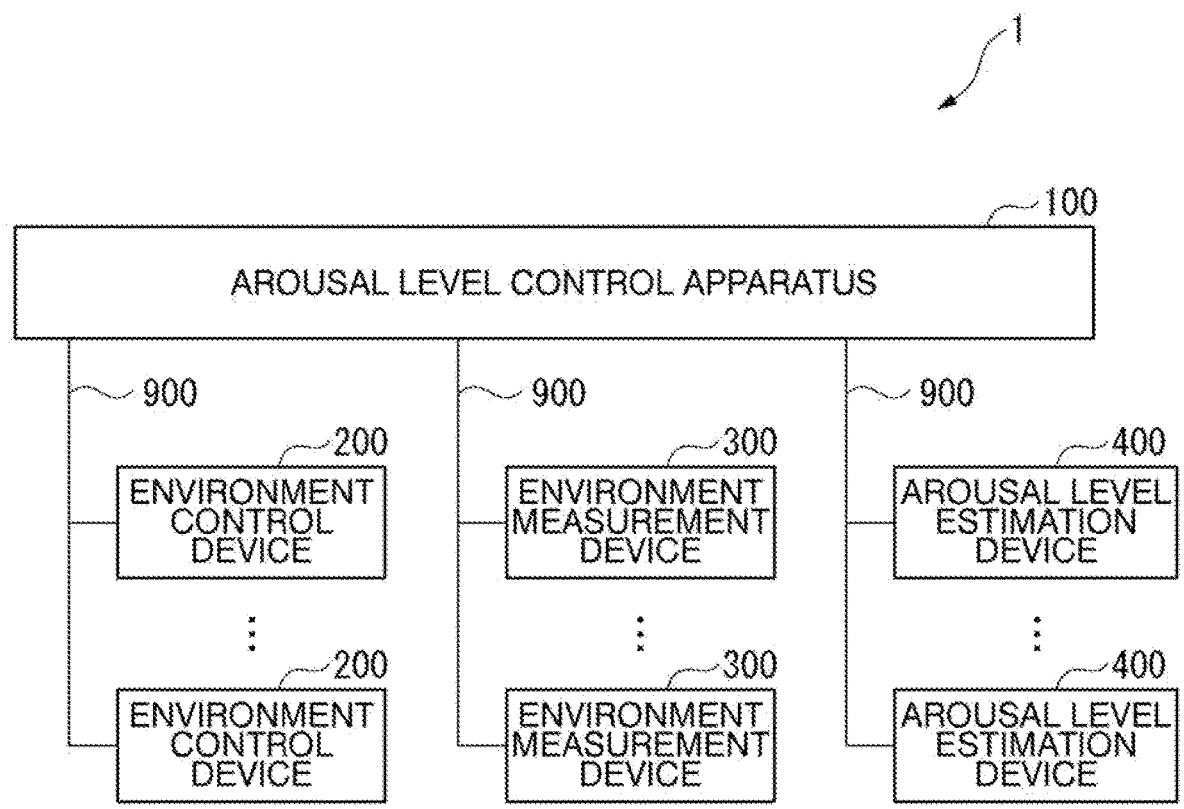
FIG. 1 is a schematic block diagram showing an example of a device configuration of an arousal level control system according to an example embodiment.

FIG. 1 is a schematic block diagram showing an example of a device configuration of an arousal level control system 1 according to an example embodiment. In the configuration shown in FIG. 1, the arousal level control system 1 includes an arousal level control apparatus 100, one or more environment control devices 200, one or more environment measurement devices 300, and one or more arousal level estimation devices 400.

The arousal level control apparatus 100 is connected to each of the environment control devices 200, each of the environment measurement devices 300, and each of the arousal level estimation devices 400 via a communication line 900, and can communicate with these devices. The communication line 900 may be configured with any of form such as the access method of a communication line such as a dedicated line, the Internet, a VPN (Virtual Private Network), a LAN (Local Area Network) and the physical form of the communication line such as a wired line or a wireless line.

The arousal level control system 1 determines the arousal level of the subject of arousal level control, and controls the physical quantity of the surrounding environment of the subject of the arousal level control according to the determination result, to maintain or improve the arousal level. As mentioned above, the arousal level is an index indicating the degree of awakeness, and it indicates that the lower the arousal level, the drowsier the arousal control subject is.

The subject of arousal control may also be referred to as a user or simply as a subject.

Here, the physical quantity of the surrounding environment where the subject is present is a physical quantity (a quantity in a physical sense) that affects a subject, and, in this case, is a physical quantity that affects the arousal level of the subject in particular. The physical quantity of the surrounding environment where the subject is present is also simply referred to as a physical quantity.

Examples of physical quantities include, but are not limited to, ambient temperature such as room temperature and brightness such as illuminance of lighting equipment. For example, the arousal level control system 1 may give the subject stimuli other than temperature and brightness, such as humidity (dampness), sound or vibration, in addition to or instead of temperature and brightness. Moreover, the arousal level control system 1 may use a measure such as humidity (dampness), sound, or vibration as a physical quantity.

Hereinafter, the ambient temperature is simply referred to as temperature. However, the arousal level control system 1 may control other temperatures in addition to or instead of ambient temperature. For example, the arousal level control system 1 may control the temperature of a matter that is in direct contact with the subject. As a specific example, a heater may be provided on the seat surface of the subject's seat, and the arousal level control system 1 may control the temperature of the heater.

The unit by which the arousal level control system 1 controls physical quantities is not limited to a specific one. For example, a spot-type air conditioning device (a local air conditioner) and a lighting stand may be installed at the seat of a person, and the arousal level control system 1 may control physical quantities on a seat-by-seat basis. Alternatively, the arousal level control system 1 may control physical quantities on a room-by-room basis, or may control physical quantities of an entire building. Moreover, when controlling the physical quantities of an entire building, subjects need not be everyone in the building, but may be some of them in the building.

The number of subjects may be one or may be more than one. Only specific persons may become subjects by the arousal level control system 1 accepting registration of subjects, for example. Alternatively, unspecified persons located in a control target space of the arousal level control system 1 may become subjects. In a case where there are a plurality of subjects, the arousal level control system 1 may control physical quantities for each subject, or may commonly control physical quantities of the plurality of subjects.

In order to improve the arousal level of a subject, it is conceivable to control a physical quantity so as to decrease the comfort, depending on the person, by raising the room temperature or brightening the lighting for example. The arousal level control system 1 determines the arousal level of the arousal level control subject and controls physical quantities according to the determination result, so that it is possible to achieve a balance between ensuring the arousal level and the comfort of the subject. For example, the arousal level control system 1 may control physical quantities only when the arousal level of the subject decreases.

In the following description, a case where the arousal level control system 1 improves the arousal level (shakes off drowsiness) of a subject is taken as an example; however, it is not limited to such an example. For example, the arousal level control system 1 may decrease the arousal level of (induce sleep in) a subject. For example, the arousal level control system 1 may switch between executing control for improving arousal level and executing control for reducing arousal level, depending on the time period. Alternatively, in a case where a subject's arousal level is predicted to decrease, the arousal level control system 1 may execute control so that the subject's arousal level does not decrease (that is to say, the subject does not become drowsy). Or, in a case where a subject's arousal level is predicted to improve, the arousal level control system 1 may execute control so that the subject's arousal level does not improve (that is to say, the subject is not aroused).

The arousal level control apparatus 100 controls the environment control device 200 according to the arousal level of the subject. The arousal level control apparatus 100 controls the physical quantity of the surrounding environment where the subject is present by controlling the environment control device 200, thereby controlling the arousal level of the subject.

The arousal level control apparatus 100 is configured, using a computer such as a personal computer and a workstation, for example.

The environment control device 200 is a device that adjusts a physical quantity. As mentioned above, examples of physical quantities include ambient temperature and illuminance. Temperature can be adjusted by an air conditioning device, and illuminance can be adjusted by a lighting device. As described above, examples of the environment control device 200 include, but are not limited to, an air conditioning device and a lighting device.

The environment control device 200 corresponds to an example of a control target device, and is controlled by the arousal level control apparatus 100 as mentioned above.

A device other than the environment control device 200, such as the arousal level control apparatus 100, can acquire information on the operating state such as a device setting value from the environment control device 200, and can update the device setting value for the environment control device 200. Here, the device setting value is a physical quantity set in the environment control device 200 as a control target value. The device setting value may also be referred to as a physical quantity setting value or simply a setting value.

When the environment control device 200 is an air conditioning device, a set temperature can be used as a device setting value. When the environment control device 200 is a lighting device, a lighting output (such as light intensity, illuminance, electric current value, and electric power value) can be used as a device setting value. In the following description, a case where illuminance is used as a device setting value of the lighting device is taken as an example, but it is not limited to such an example.

The environment measurement device 300 is a device that measures physical quantities such as temperature and illuminance and converts them into numerical data. Examples of the environment measurement device 300 include, but are not limited to, a temperature sensor and an illuminance sensor.

The arousal level estimation device 400 is a device that estimates the arousal level of a subject from physiological information and the like and converts it into numerical data. The arousal level estimation device 400 may use any one or a combination of body temperature, video of a face, and pulse wave as physiological information; however, it is not limited to this example. The arousal level estimation device 400 measures or calculates physiological information, and converts the obtained physiological information into a numerical value (arousal level) indicating the degree of arousal.

The arousal level estimation device 400 is not essential for the arousal level control system 1. When the arousal level control system 1 does not include the arousal level estimation device 400, the arousal of the subject is estimated on the basis of a physical quantity.

Next, a functional configuration of the arousal level control apparatus 100 will be described.

Figure 2:
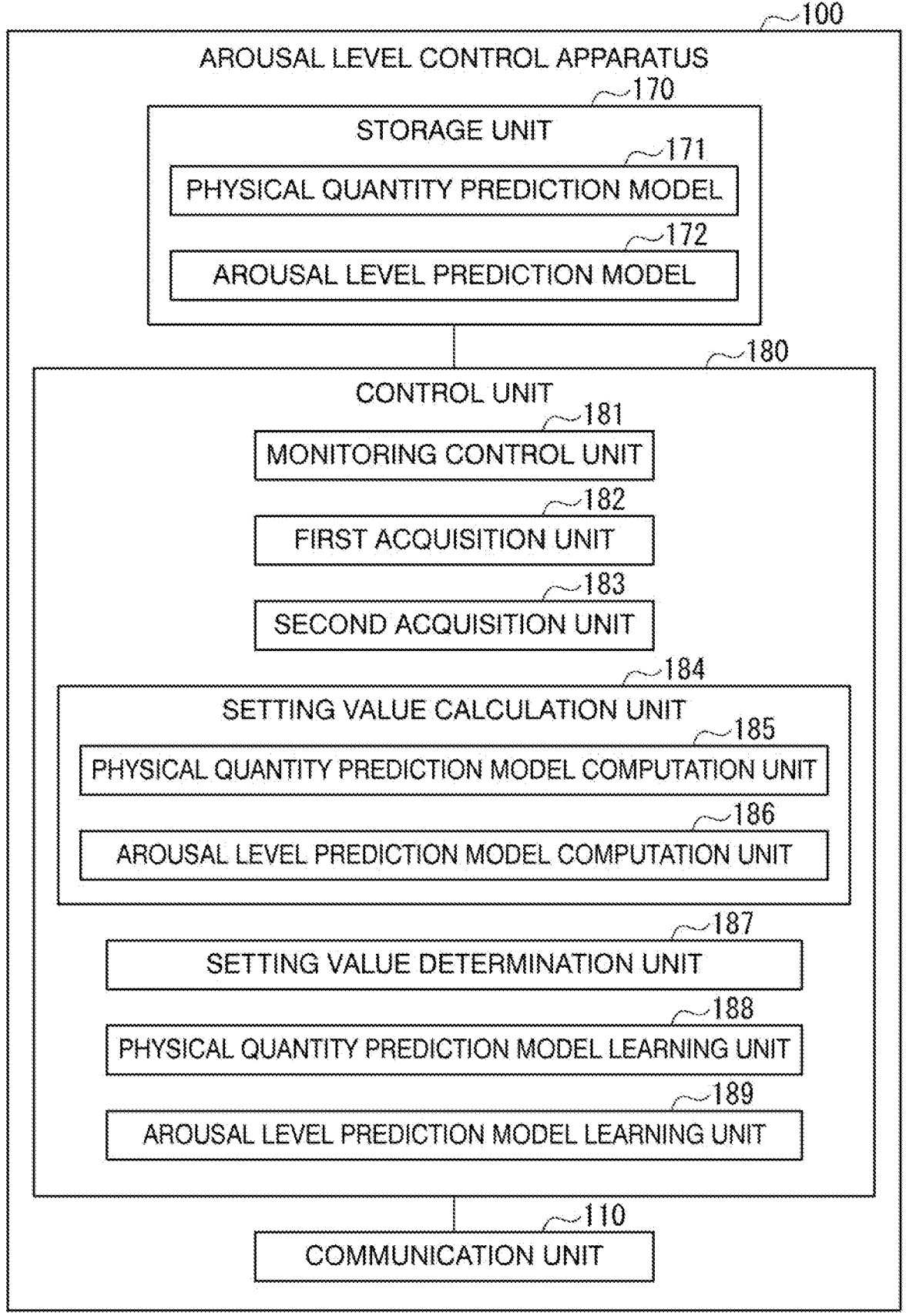
FIG. 2 is a schematic block diagram showing an example of a functional configuration of an arousal level control apparatus according to the example embodiment.

FIG. 2 is a schematic block diagram showing an example of a functional configuration of the arousal level control apparatus 100. In the configuration shown in FIG. 2, the arousal level control apparatus 100 includes a communication unit 110, a storage unit 170, and a control unit 180. The storage unit 170 includes (stores) a physical quantity prediction model 171 and an arousal level prediction model 172. The control unit 180 includes a monitoring control unit 181, a first acquisition unit 182, a second acquisition unit 183, a setting value calculation unit 184, a physical quantity prediction model computation unit 185, an arousal level prediction model computation unit 186, a setting value determination unit 187, a physical quantity prediction model learning unit 188, and an arousal level prediction model learning unit 189.

The communication unit 110 communicates with other devices according to the control of the control unit 180. In particular, the communication unit 110 receives various information from each of the environment control device 200, the environment measurement device 300, and the arousal level estimation device 400. Moreover, the communication unit 110 transmits device setting values to the environment control device 200.

The storage unit 170 stores various information. The storage unit 170 is configured using a memory storage device included in the arousal level control apparatus 100.

The physical quantity prediction model 171 is a mathematical model for calculating a predicted value of a physical quantity on the basis of a setting value of the physical quantity (device setting value).

More specifically, the physical quantity prediction model 171, on the basis of the measurement value of the physical quantity measured by the environment measurement device 300 and the setting value of the physical quantity set in the environment control device 200, calculates a predicted value of the physical quantity at a time at which a predetermined amount of time has elapsed.

The time at which the above predetermined amount of time has elapsed is the time at which the predetermined amount of time has elapsed since the time at which the physical quantity given to the physical quantity prediction model 171 was measured. Instead of the measurement time of the physical quantity given to the physical quantity prediction model 171, the time at which the arousal level control apparatus 100 (communication unit 110) has received the physical quantity can be used.

The above predetermined amount of time may be a certain fixed amount of time or may be variable as a model parameter. The model parameter referred to here is a setting parameter of the physical quantity prediction model 171. The value of a model parameter is referred to as model parameter value.

The arousal level prediction model 172 is a mathematical model for calculating a predicted value of an arousal level on the basis of a predicted value of the physical quantity calculated by the physical quantity prediction model 171. Furthermore, the arousal level prediction model 172 calculates a predicted value of an arousal level on the basis of a variation in a physical quantity in addition to a predicted value of the physical quantity. More specifically, the arousal level prediction model 172 uses the history of predicted values of the physical quantity calculated by the physical quantity prediction model 171, and calculates the predicted value of the variation in the arousal level of the subject at the time when the predetermined amount of time has elapsed, on the basis of the time average value and the variation in the physical quantity.

The arousal level prediction model 172 may calculate the predicted value of the arousal level at least on the basis of the temporal variance in the arousal level.

The control unit 180 controls each unit of the arousal level control apparatus 100 and executes various processes. The control unit 180 is realized by a CPU (Central Processing Unit) included in the arousal level control apparatus 100 reading out a program from the storage unit 170 and executing the program.

The monitoring control unit 181 communicates with the environment control device 200 via the communication unit 110. In communication with the environment control device 200, the monitoring control unit 181 acquires a device setting value set in the environment control device 200. Moreover, the monitoring control unit 181 updates the device setting value of the environment control device 200 by communicating with the environment control device 200. For example, the monitoring control unit 181 communicates with the environment control device 200 at constant intervals, and saves the device setting value acquired by the communication, together with the timestamp of the time of acquisition thereof (of the time of reception thereof). The term save here means, for example, causing the storage unit 170 to store the device setting value and the timestamp therein.

In this manner, the monitoring control unit 181 sets a device setting value in the control target device. The monitoring control unit 181 corresponds to an example of a setting unit (setting means).

The monitoring control unit 181 sets, as the device setting value, the device setting value calculated by the setting value calculation unit 184 or the device setting value determined by the setting value determination unit 187 in the environment control device 200. In the case where the setting value calculation unit 184 can calculate a device setting value and the calculated device setting value satisfies a predetermined condition (the calculated device setting value is greater than or equal to a predetermined condition), that is, the calculated device setting value is determined as being highly accurate, the monitoring control unit 181 sets the device setting value calculated by the setting value calculation unit 184 in the environment control device 200. On the other hand, in the case where the setting value calculation unit 184 cannot calculate a device setting value or the device setting value calculated by the arousal level control system 1 does not satisfy a predetermined condition, that is, the calculated device setting value is determined as being of low accuracy, the monitoring control unit 181 sets the device setting value determined by the setting value determination unit 187 in the environment control device 200.

For example, in the case where the setting parameter value of the physical quantity prediction model 171 has not been set, it is conceivable that the physical quantity prediction model 171 cannot calculate the predicted value of the physical quantity, and thus the setting value calculation unit 184 cannot calculate the device setting value. Moreover, in the case where the setting parameter value of the arousal level prediction model 172 has not been set, it is conceivable that the arousal level prediction model 172 cannot calculate the predicted value of the arousal level, and thus the setting value calculation unit 184 cannot calculate the device setting value.

Moreover, in the case where the accuracy of prediction of the physical quantity by the physical quantity prediction model 171 has decreased below a predetermined condition, it is conceivable that the accuracy of the device setting value calculated by the setting value calculation unit 184 thus decreased. Also, in the case where a predetermined amount of time or more has elapsed since having set the setting parameter value of the physical quantity prediction model 171, it is conceivable that the accuracy of prediction of the physical quantity by the physical quantity prediction model 171 decreases, and thus the accuracy of the device setting value calculated by the setting value calculation unit 184 decreases.

Moreover, in the case where the accuracy of prediction of the arousal level by the arousal level prediction model 172 has become lower than a predetermined condition, it is conceivable that the accuracy of the device setting value calculated by the setting value calculation unit 184 thus decreases. Also, in the case where a predetermined amount of time or more has elapsed since having set the setting parameter value of the arousal level prediction model 172, it is conceivable that the accuracy of prediction of the arousal level by the arousal level prediction model 172 decreases, and thus the accuracy of the device setting value calculated by the setting value calculation unit 184 decreases.

In some or all of these cases, the monitoring control unit 181 may set the device setting value determined by the setting value determination unit 187 in the environment control device 200.

The first acquisition unit 182 communicates with the environment measurement device 300 via the communication unit 110, and acquires the measurement value of the physical quantity measured by the environment measurement device 300. For example, the first acquisition unit 182 communicates with the environment measurement device 300 at constant intervals, and saves the measurement value of the physical quantity acquired by the communication, together with the timestamp of the time of acquisition thereof (of the time of reception thereof). This timestamp can be interpreted as indicating the time at which the physical quantity is measured by the environment measurement device 300.

The second acquisition unit 183 communicates with the arousal level estimation device 400 and acquires an estimated value of the arousal level of the subject. For example, the second acquisition unit 183 communicates with the arousal level estimation device 400 at constant intervals, and saves the estimated value of the arousal level acquired by the communication, together with the timestamp of the time of acquisition thereof (of the time of reception thereof). This timestamp can be interpreted as indicating the time at which the estimation of the arousal level is made by the arousal level estimation device 400.

The estimated value of the arousal level of the subject is also referred to as arousal level estimated value.

The setting value calculation unit 184 calculates a device setting value of the environment control device 200 for improving the arousal level of a user. For example, the setting value calculation unit 184 calculates a device setting value at constant intervals. The setting value calculation unit 184 acquires a device setting value from the monitoring control unit 181, acquires a measurement value of a physical quantity from the first acquisition unit 182, acquires an arousal level estimated value from the second acquisition unit 183, and calculates a device setting value on the basis of these values. The setting value calculation unit 184 outputs the calculated device setting value to the monitoring control unit 181. The monitoring control unit 181 transmits the device setting value acquired from the setting value calculation unit 184 to the environment control device 200 via the communication unit 110, to thereby set the device setting value in the environment control device 200.

The setting value calculation unit 184 solves (or approximately solves) an optimization problem under a constraint condition related to physical quantities using the physical quantity prediction model 171 and the arousal level prediction model 172, and there thereby calculates a setting value for controlling the arousal level of the subject. The setting value calculation unit 184 calculates, by solving (or by approximately solving) the optimization problem, the device setting value so that the arousal level becomes even higher. As described above, the process in which the setting value calculation unit 184 solves the optimization problem corresponds to an example of a process of making an objective function value such as arousal level even higher (or even lower, or even closer to the target value). The setting value calculation unit 184 may calculate, by solving (or by approximately solving) the optimization problem, the device setting value in the case where the arousal level is the highest.

In the optimization problem solved by the setting value calculation unit 184, the physical quantity prediction model 171 is used as a first constraint condition, the arousal level prediction model 172 is used as a second constraint condition, and the condition where the device setting value of the environment control device 200 is within a predetermined range is used as a third constraint condition. The setting value calculation unit 184 solves the optimization problem that includes these constraint conditions. The predetermined range of the device setting value here is an allowed range defined by the specification of the environment control device 200.

The objective function of the optimization problem solved by the setting value calculation unit 184 is, for example, a function that calculates the sum value or average value of predicted values of the variation in arousal level of one or more (or two or more) subjects within one or more time steps. The setting value calculation unit 184 solves the optimization problem so as to make the value of this objective function greater, to calculate the device setting value. The setting value calculation unit 184 may calculate the device setting value in the case where this objective function is the maximum. The sum value of the predicted values of the variation in arousal level may be the sum of the predicted values of the variation in arousal level for the respective subjects. The average value of the predicted values of the variation in arousal level may be the value obtained by dividing the sum of the predicted values of the variation in arousal level for the respective subjects by the number of subjects.

The optimization problem solved by the setting value calculation unit 184 is referred to as an arousal level optimization model. The arousal level optimization problem is configured as a mathematical model.

The setting value calculation unit 184 may calculate the setting value so that the trimmed mean of the predicted values of the variation in arousal level becomes even greater for one or more subjects and in one or more time steps.

As a result of the setting value calculation unit 184 using the trimmed mean, for example, when there are persons having an extremely small or, in contrast, an extremely large variation in the arousal level with respect to the variation in physical quantity, these subjects will not be over-evaluated, and thus the overall optimization can be achieved. Alternatively, this optimization may be performed for some subjects.

The setting value calculation unit 184 may solve an optimization problem that includes a constraint condition regarding the comfort score calculated for the device setting value, to calculate the device setting value that satisfies this constraint condition. For example, the setting value calculation unit 184 may calculate each of a plurality of types of devices setting values so that the sum of the comfort penalty scores calculated for each of the plurality of types of device setting values falls within a predetermined range. In other words, the setting value calculation unit 184 may calculate each of the plurality of types of device setting values when a condition is satisfied such that the comfort score is within a certain range.

As described above, with the setting value calculation unit 184 calculating device setting values so that the constraint condition regarding comfort is satisfied, it is possible to prevent the comfort from extremely decreasing.

The physical quantity prediction model computation unit 185 reads out the physical quantity prediction model 171 from the storage unit 170 and executes it. Therefore, the physical quantity prediction model computation unit 185 executes physical quantity prediction using the physical quantity prediction model 171.

The arousal level prediction model computation unit 186 reads out the arousal level prediction model 172 from the storage unit 170 and executes it. Therefore, the arousal level prediction model computation unit 186 executes arousal level prediction using the arousal level prediction model 172.

When the setting value calculation unit 184 cannot calculate a device setting value that yields a high awakening effect, the setting value determination unit 187, in place of the setting value calculation unit 184, calculates the device setting value and outputs it to the monitoring control unit 181. One of the purposes of this is, as described later, to generate learning data so that the physical quantity prediction model learning unit 188 and the arousal level prediction model learning unit 189 can efficiently perform learning.

The physical quantity prediction model learning unit 188 sets or updates the physical quantity prediction model 171 by acquiring setting parameter values of the physical quantity prediction model 171 by means of machine learning or the like. The physical quantity prediction model learning unit 188 performs machine learning or the like at least in any one of the cases: where the setting parameter value of the physical quantity prediction model 171 has not been set; where the accuracy of prediction made by the physical quantity prediction model 171 has decreased below a predetermined condition; and where a predetermined amount of time or more has elapsed since setting the setting parameter values of the physical quantity prediction model 171.

As learning data, the physical quantity prediction model learning unit 188 acquires a device setting value from the monitoring control unit 181, and acquires a measurement value of a physical quantity from the first acquisition unit 182. The physical quantity prediction model learning unit 188 performs machine learning or the like on the basis of the measurement value of the physical quantity and the setting value (device setting value) of the physical quantity, to acquire the setting parameter value of the physical quantity prediction model 171. The physical quantity prediction model learning unit 188 outputs the parameter value of the physical quantity prediction model 171 obtained by machine learning or the like to the setting value calculation unit 184 and the setting value determination unit 187.

The arousal level prediction model learning unit 189 sets or updates the arousal level prediction model 172 by acquiring setting parameter values of the arousal level prediction model 172 by mean of machine learning or the like.

The arousal level prediction model learning unit 189 performs machine learning or the like at least in any one of the cases: where the setting parameter value of the arousal level prediction model 172 has not been set; where the accuracy of prediction made by the arousal level prediction model 172 has become lower than a predetermined condition; and where a predetermined amount of time or more has elapsed since setting the setting parameter values of the arousal level prediction model 172.

The arousal level prediction model learning unit 189 is not essential for the arousal level control apparatus 100. In particular, in the case where the arousal level control system 1 does not include the arousal level estimation device 400, the arousal level control apparatus 100 does not acquire information on arousal level from the outside, and therefore correct data in arousal level machine leaning cannot be obtained. In such a case, a configuration may be considered in which the arousal level control apparatus 100 does not include the arousal level prediction model learning unit 189. If the arousal level prediction model learning unit 189 is not included, there may be considered an operation such that the arousal level control apparatus 100 continues to use the arousal level prediction model 172 in an unchanged manner, and when it becomes necessary to update the arousal level prediction model 172, an administrator or the like of the arousal level control system 1 manually updates it. Alternatively, the arousal level control apparatus 100 may automatically update the model parameter value by a method such as acquiring the latest model parameter value via the Internet.

As learning data, the arousal level prediction model learning unit 189 acquires a measurement value of the physical quantity from the first acquisition unit 182, and acquires an arousal level estimated value from the second acquisition unit 183. The arousal level prediction model learning unit 189 performs machine learning or the like on the basis of the measurement value of the physical quantity and the arousal level (estimated value), to acquire the setting parameter value of the arousal level prediction model 172.

The following describes an example of a specific calculation procedure for each of the setting value calculation unit 184, the setting value determination unit 187, the physical quantity prediction model learning unit 188, and the arousal level prediction model learning unit 189.

First, described here is an example of an arousal optimization model (optimization problem) used by the setting value calculation unit 184 to calculate a device setting value. The setting value calculation unit 184 calculates a device setting value by executing a mathematical optimization calculation for this arousal optimization model.

This arousal optimization model uses the following constants, coefficients, variables, and functions.

Decision Variable $T_t^{set}$: Air conditioning temperature setting value in time step t
$L_t^{set}$: Lighting output setting value in time step t A decision variable is a variable whose value is calculated by the setting value calculation unit 184 in the optimizing computation. In the case of the example described here, the setting value calculation unit 184 calculates, by solving the optimization problem, the temperature to be set in the environment control device 200 serving as an air conditioning device and the illuminance to be set in the environment control device 200 serving as a lighting device.

Dependent Variable $A^A$: Average of predicted values of variation in arousal level for subjects and in time steps
$A_i^A$: Average of predicted values of variation in arousal level of subject i in time steps
$A_{i,t}^A$: Predicted value of variation in arousal level of subject i in time step t
$T_t$: Predicted value of temperature in time step t
$T_t^A$: Predicted value of temporal variation in temperature in time step t Note that the variation in one time step before the time step t, that is, from the time step t-1 to t is referred to as variation in the time step t. The variation over time is a variation observed over time (temporal variation).

$L_t$: Predicted value of illuminance in time step t
$L_t^A$: Predicted value of temporal variation in illuminance in time step t
$T_t^{pnlty}$: Degree of deviation from comfort value of air conditioning temperature setting value in time step t
$L_t^{pnlty}$: Degree of deviation from comfort value of lighting output setting value in time step t
$A_{i,t}^\sigma$: Degree of variance of temporal variation in arousal level of subject i in time step t Constant/Coefficient T: Set of indexes of time steps
N: Set of indexes of subjects
$T^{min}$: Lower limit value of air conditioning temperature setting value
$T^{max}$: Upper limit value of air conditioning temperature setting value
$L^{min}$: Lower limit value of lighting output setting value
$L^{max}$: Upper limit value of lighting output setting value
$T^{best}$: Comfort value of air conditioning temperature setting value
$p_T$: Penalty coefficient of air conditioning temperature
$L^{best}$: Comfort value of lighting output setting value
$p_L$: Penalty coefficient of lighting output
$P^{max}$: Upper limit value of penalty score
$a_i(\tau)$: Arousal level estimated value of subject i at relative time $\tau$
$\Delta\tau$: Time step width Function $f_A$: Arousal level variation prediction function (arousal level prediction model)
$f_T$: Temperature prediction function (one of physical quantity prediction models)
$f_L$: Illuminance prediction function (one of physical quantity prediction models)

Index t: Index of time step
i: Index of subject

The objective function of this arousal optimization model is expressed as Equation (1).

[Equation 1]

$$\underset{T_t^{set}, L_t^{set}, t \in \mathcal{J}}{\text{maximize}} \; A^\Delta \quad (1)$$

$A^\Delta$ (average of predicted values of variation in arousal level for subjects and time steps) is expressed as Equation (2).

[Equation 2]

$$A^\Delta = \underset{i \in N}{(\text{mean})} A_i^\Delta \quad (2)$$

$A_i^\Delta$ (average of predicted values of variation in arousal level of subject i for time steps) is expressed as Equation (3).

[Equation 3]

$$A_i^\Delta = \underset{t \in \mathcal{J}}{\text{mean}} A_{i,t}^\Delta \quad (3)$$

The constraint condition where the device setting value of the air conditioning device among the environment control devices 200 is within a predetermined range is expressed as Equation (4).

[Equation 4]

$$T^{min} \le T_t^{set} \le T^{max} \quad (4)$$

The constraint condition where the device setting value of the lighting device among the environment control devices 200 is within a predetermined range is expressed as Equation (5).

[Equation 5]

$$L^{min} \le L_t^{set} \le L^{max} \quad (5)$$

The constraint condition of the physical quantity prediction model 171 regarding temperature is expressed as Equation (6).

[Equation 6]

$$T_t = f_T(T_{t-1}, T_t^{set}) \quad (6)$$

The constraint condition of the physical quantity prediction model 171 regarding illuminance is expressed as Equation (7).

[Equation 7]

$$L_t = f_L(L_{t-1}, L_t^{set}) \quad (7)$$

The constraint conditions of these physical quantity prediction models 171 show physical constraint conditions related to the operation of the environment control devices 200, such as a delay between the moment of setting the device setting value in the environment control device 200 and the moment at which the physical quantity actually reaches the device setting value.

Therefore, as explanatory variables, the physical quantity prediction model 171 includes a parameter indicating a physical quantity in the surrounding environment that affects arousal level of a subject and a parameter indicating a setting value of a control device that affects the physical quantity. Moreover, an explained variable of the physical quantity prediction model 171 is a parameter indicating the predicted value of the physical quantity. Equation (6) and Equation (7) are exemplified by explicit functions in which the value of an explained variable is calculated by applying the predetermined processing shown by the physical quantity prediction model 171 to the value of the explanatory variable. Note that Equation (6) and Equation (7) do not necessarily have to be expressed by explicit functions.

The constraint condition of the arousal level prediction model 172 is expressed as Equation (8).

[Equation 8]

$$A_{i,t}^\Delta = f_A(T_t, T_t^\Delta, L_t, L_t^\Delta) \quad (8)$$

Therefore, as explanatory variables, the arousal level prediction model 172 includes a parameter indicating a physical quantity and a parameter indicating the temporal variation therein. Moreover, an explained variable of the arousal level prediction model 172 is a parameter indicating the predicted value of temporal variation in the arousal level. Equation (8) is exemplified by an explicit function in which the value of an explained variable is calculated by applying the predetermined processing shown by the arousal level prediction model 172 to the value of the explanatory variable. Note that Equation (8) does not necessarily have to be expressed by an explicit function.

The constraint condition of the arousal level prediction model 172 indicates how the arousal level of a subject changes with respect to physical quantities and variation therein.

$T_t^\Delta$ (predicted value of temporal variation in temperature in time step t) is expressed as Equation (9).

[Equation 9]

$$T_t^\Delta = |T_t - T_{t-1}| \quad (9)$$

$L_t^\Delta$ (predicted value of temporal variation in illuminance in time step t) is expressed as Equation (10).

[Equation 10]

$$L_t^\Delta = |L_t - L_{t-1}| \quad (10)$$

Under the constraint conditions shown by Equations (2) to (10), the setting value calculation unit 184 solves a mathematical programming problem for obtaining a decision variable that maximizes the objective function indicating the average value of arousal level temporal variation predicted values for all users and for all time steps, shown in Equations (1) to (3). As a result, the setting value calculation unit 184 calculates a device setting value (decision variable value). It can be said that the process executed by the setting value calculation unit 184 is, for example, a process of calculating a setting value so that the value of the objective function is maximized under the constraint condition by using the arousal optimization model as described above. The process executed by the setting value calculation unit 184 is not necessarily limited to being a process in the case where the value of the objective function is maximum, and may be a process of calculating a setting value in the case where the value of the objective function becomes large, for example.

As described above, Equations (6) and (7) are constraint conditions related to the physical quantity prediction model 171. Equations (8) to (10) are constraint conditions related to the arousal level prediction model 172. Equations (4) and (5) are constraint conditions where the device setting value of the environment control devices 200 is within a predetermined range.

Here is described options of the arousal optimization model (optimization problem) used by the setting value calculation unit 184.

A trimmed mean may be used as $A^\Delta$ (average of predicted values of variation in arousal level for subjects and in time steps). In such a case, Equation (11) is used instead of Equation (2).

[Equation 11]

$$A^\Delta = \underset{i \in N}{trimmedmean}\ A_i^\Delta \tag{11}$$

That is to say, the objective function may be a combination of Equations (1), (3), and (11) instead of Equations (1) to (3). Here, trimmed mean indicates a trimmed mean. A trimmed mean is an arithmetic average obtained regarding the data that remains after discarding data at a predetermined ratio from both ends of the data arranged in order of size. As a result, subjects whose arousal level changes extremely or does not change at all can be excluded from the numerical calculation of the objective function, so that it is possible to prevent a device setting value that excessively suits for a small number of specific subjects from being calculated.

That is to say, as a result of the setting value calculation unit 184 using the trimmed mean, for example, when there are persons having an extremely small or, in contrast, an extremely large variation in the arousal level with respect to the variation in physical quantity, these subjects will not be over-evaluated, and thus the overall optimization can be achieved.

A preferred truncation ratio (the ratio of both ends combined) in the trimmed mean is 10%.

The constraint condition related to comfort may be included in the constraint conditions so that the comfort for the subjects will not decrease significantly. For example, the comfort penalty score constraint condition shown in Equation (12) may be included.

[Equation 12]

$$p_T T_t^{pnlty} + p_L L_t^{pnlty} \leq P^{max} \tag{12}$$

$T_t^{pnlty}$ (degree of deviation from comfort value of air conditioning temperature setting value in time step t) is expressed as Equation (13).

[Equation 13]

$$T_t^{pnlty} = |T_t^{set} - T^{best}| \tag{13}$$

$L_t^{pnlty}$ (degree of deviation from comfort value of lighting output setting value in time step t) is expressed as Equation (14).

[Equation 14]

$$L_t^{pnlty} = |L_t^{set} - L^{best}| \tag{14}$$

Equations (12) to (14) indicate the constraint condition that the sum of the comfort penalty scores is within a predetermined range (less than or equal to a predetermined value). In other words, it is a constraint condition that air conditioning and lighting do not simultaneously take device setting values that cause discomfort. This has an effect of avoiding a situation where, for a plurality of environment control devices such as an air conditioning device and a lighting device, the device setting values simultaneously depart from those that provide the most comfortable environment.

The effect of including Equations (12) to (14) in the constraint conditions will be described, with reference to FIG. 3 and FIG. 4.

Figure 3:
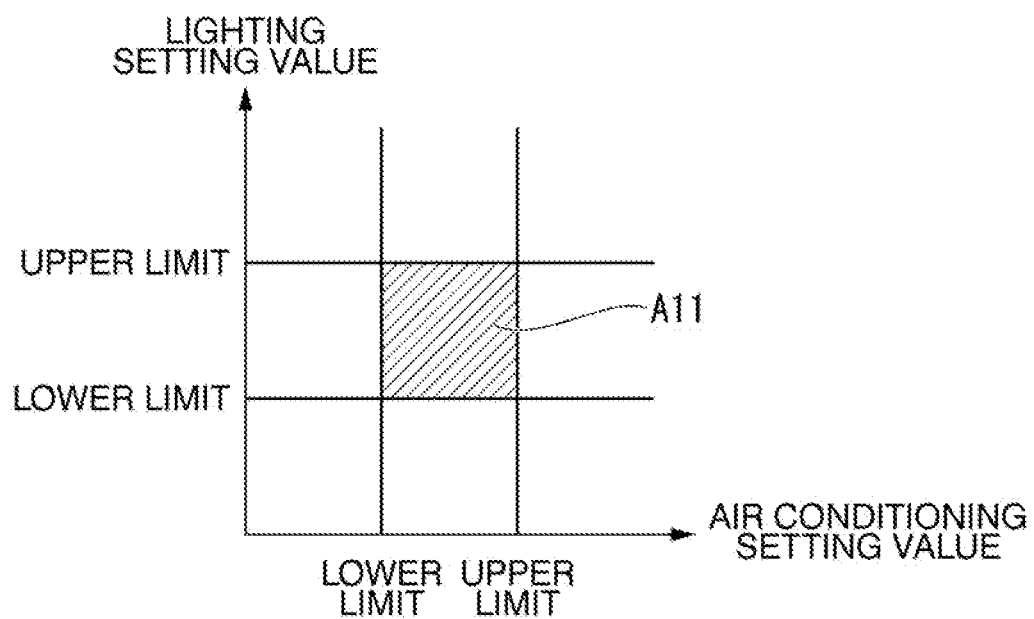
FIG. 3 is a diagram showing an example of device setting values when a predetermined constraint condition is not included in an arousal level optimization model used by a setting value calculation unit according to the example embodiment.

FIG. 3 is a diagram showing an example of device setting values when the constraint conditions of Equation (12) to (14) are not included in the arousal level optimization model used by the setting value calculation unit 184. The horizontal axis of the graph in FIG. 3 represents air conditioning setting values (air conditioning temperature setting values (temperature)). The vertical axis represents lighting setting values (lighting output setting value (illuminance)).

In the example of FIG. 3, the device setting value can be set arbitrarily within a range that satisfies the constraint condition that the temperature is within the range between the upper limit value and the lower limit value of the temperature that can be set in the air conditioning device, and also the constraint condition that the illuminance is within the range between the upper limit value and the lower limit value that can be set in the lighting device. The region A11 (shaded region) indicates the range that satisfies the constraint conditions.

It is conceivable that the comfort level for the subject is relatively low in the neighborhood of the upper limit value or the lower limit value of each of the air conditioning setting value and the lighting setting value. Therefore, in the case where both the air conditioning setting value and the lighting setting value are set near the upper limit value or the lower limit value thereof, it is conceivable that the comfort level decreases significantly for the subject as a result of the reduction in the temperature comfort and the reduction in the illuminance comfort being combined.

Figure 4:
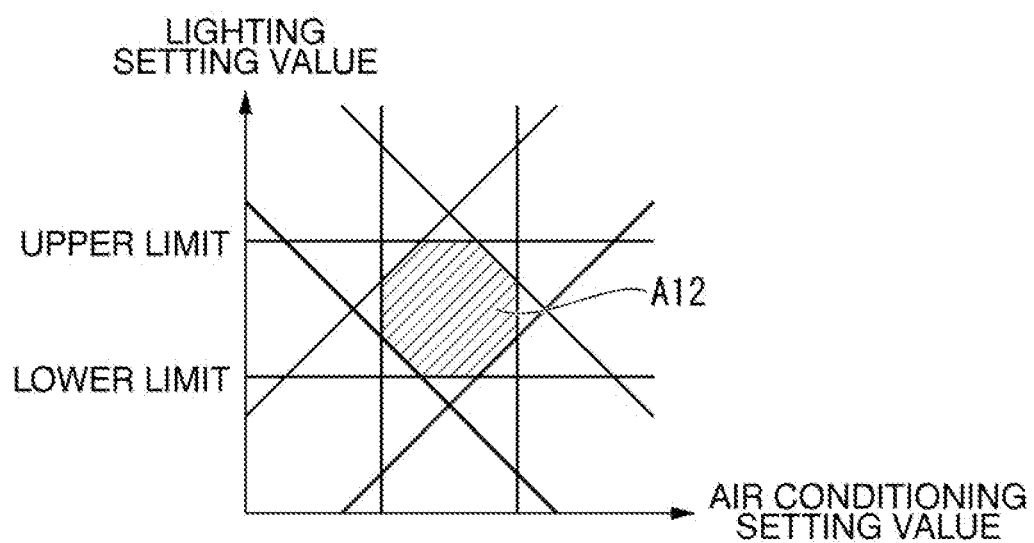
FIG. 4 is a diagram showing an example of device setting values when a predetermined constraint condition is included in the arousal level optimization model used by the setting value calculation unit according to the example embodiment.

FIG. 4 is a diagram showing an example of device setting values when the predetermined constraint conditions of Equation (12) to (14) are included in the arousal level optimization model used by the setting value calculation unit 184. The horizontal axis of the graph in FIG. 4 represents air conditioning setting values (air conditioning temperature setting value (temperature)). The vertical axis represents lighting setting values (lighting output setting value (illuminance)).

In the example of FIG. 4, in addition to the constraint condition in the case of FIG. 3, there is provided a constraint condition that the total magnitude of deviation of the air conditioning setting value from the comfort value and deviation of the lighting setting value from the comfort value is less than or equal to a predetermined magnitude. The region A12 (shaded region) indicates the range that satisfies the constraint conditions. As a result, even within the range of the air conditioning setting value and the lighting setting value that can be set in both the air conditioning device and the lighting device, device setting values will not be set to the device setting values that significantly deviate from the comfort values. As a result, it is possible to avoid a large reduction in the comfort level for the subject caused by the combination of a reduction in the temperature comfort and a reduction in the illuminance comfort.

Comparing FIG. 3 and FIG. 4, the effect of adding the constraint conditions of Equations (12) to (14) is schematically illustrated by the range region of device setting value changing from the region A11 (shaded region) in FIG. 3 to the region A12 (shaded region) in FIG. 4.

In the case where the arousal level estimated value can be acquired from by the second acquisition unit 183, Equation (15) may be used instead of Equation (8).

[Equation 15]

$$A_{i,t}^{\Delta} = A_{i,t} - A_{i,t-1} \quad (15)$$

In such a case, the constraint condition may include Equation (16).

[Equation 16]

$$A_{i,t}^{\Delta} = f_A(A_{i,t-1}, A_{i,t-1}^{\Delta}, A_{i,t-1}^{\sigma}, T_t, T_t^{\Delta}, L_t, L_t^{\Delta}) \quad (16)$$

$A_{i,t-1}^{\Delta}$ of Equation (16) can be calculated using Equation (15).

Moreover, $A_{i,t}^{\sigma}$ (degree of variance of temporal variation in arousal level of subject i in time step t) is expressed as Equation (17).

[Equation 17]

$$A_{i,t}^{\sigma} = \underset{-\Delta\tau \leq \tau < 0}{\mathrm{std}} \; a_i(\tau), t \in \mathcal{T} \quad (17)$$

By using Equations (9), (10), and (15) to (17) instead of Equations (8) to (10) as the arousal level prediction model 172, the current arousal level estimated value can be incorporated, and the effect of increasing the prediction accuracy is achieved. For this reason, the arousal level prediction model includes, as explanatory variables, the temporal average value, temporal variation, and temporal variance of arousal level. Here, std represents a standard deviation, and the temporal variance is taken as the standard deviation. In addition, the future temporal variance is treated the same as the current value (Equation 17).

Input to the arousal level prediction model 172 may include the degree of variance in arousal level as with $A_{i,t}^{\sigma}$ of Equation (16) (degree of variance of temporal variation in arousal level of subject i in time step t). In the case where the degree of variance in arousal level is large, it is conceivable that the subject is drowsy and the arousal level of the subject is relatively low. Thus, since the input to the arousal level prediction model 172 includes the degree of variance in arousal level, it is expected that the current state of the arousal level can be grasped more accurately, and the prediction accuracy of the arousal level is expected to improve.

The physical quantity prediction model 171, the arousal level prediction model 172, and the arousal optimization model will be further described.

The physical quantity prediction model 171 is a mathematical model capable of calculating a predicted value of a physical quantity at a moment at which a predetermined amount of time has elapsed, on the basis of a device setting value corresponding to the measurement value of the physical quantity. The physical quantity prediction model 171 in the case where the physical quantity is temperature and the corresponding environment control device 200 is an air conditioner, is expressed as Equation (6) as described above. The physical quantity prediction model 171 in the case where the physical quantity is illuminance and the corresponding environment control device 200 is a lighting device, is expressed as Equation (7) as described above.

The physical quantity prediction model 171 may be a linear regression model or a non-linear regression model. In this case, parameter values of the model can be identified using the learning data in which input/output data are paired. Examples of non-linear regression models include decision tree, support vector regression for a non-linear kernel, and neural networks. When identifying parameter values, values identified preliminarily from learning data obtained by experiments or the like can be used as initial values. Moreover, the physical quantity prediction model learning unit 188 may update the parameters. The parameter value identification algorithm may be executed by an appropriate method according to the functional form of the model. For example, in the case of a linear regression model, parameters can be identified by means of support vector regression.

However, the configuration of the physical quantity prediction model 171 is not limited to a specific configuration, and various configurations to which machine learning can be applied can be used.

The arousal level prediction model 172 is a mathematical model capable of calculating, in the temporal average value and temporal variation amount of the physical quantity, the predicted value of the variation amount in the arousal level of a user at a moment at which a predetermined amount of time has elapsed. The arousal level prediction model in the case where the physical quantities are temperature and illuminance and the corresponding environment control devices 200 are an air conditioner and a lighting device, is expressed as Equations (8) to (10) as described above.

The arousal level prediction model 172 may be a linear regression model or a non-linear regression model. In this case, parameter values of the model can be identified using the learning data in which input/output data are paired. Examples of non-linear regression models include decision tree, support vector regression with a non-linear kernel, and neural networks. When identifying parameter values, values identified preliminarily from learning data obtained by experiments or the like can be used as initial values. Moreover, the arousal level prediction model learning unit 189 may update the parameters. The parameter value identification algorithm may be executed by an appropriate method according to the functional form of the model. For example, in the case of a linear regression model, parameters can be identified by means of support vector regression.

However, the configuration of the arousal level prediction model 172 is not limited to a specific configuration, and various configurations to which machine learning can be applied can be used.

Since the arousal level optimization model is a nonlinear discrete optimization problem, it finds a solution by executing a mathematical optimization calculation by means of a meta-heuristic algorithm such as a genetic algorithm or a discrete PSO (Particle Swarm Optimization), for example. Regarding the constraint condition of inequalities (Equations (4), (5), and (12) mentioned above), for example, the optimum solution can be calculated by using meta-heuristics in which conversion to an unconstrained optimization problem is performed by means of a penalty function method or extension is performed in combination with a ε constraint method or the like.

The numerical values of constants and coefficients will be explained.

The value of the time step width $\Delta\tau$ is, for example, an appropriate value selected from the range of 15 to 30 minutes. The value of the time step width $\Delta\tau$ is preferably 15 minutes in the light of prediction accuracy of the arousal level prediction model and the awakening effect.

The time step index set T corresponds to a prediction horizon. It is necessary to set the number of time steps to 2 or more in order to consider the stimulus of environmental change due to time change (such as warm/cold thermal stimulus). The number of time steps is preferably 3 or 4 in consideration of the balance with the amount of calculation.

The lower limit value $T^{min}$, the upper limit value $T^{max}$, and the comfort value $T^{best}$ of the air conditioning temperature setting value may be set by the user by providing an input interface. The user may be asked to input each of the three values. The user may be asked to input the comfort value $T^{best}$ only, and the remaining two values may be set to a temperature 1° C. lower or higher than that does not impair comfort, that is, "$T^{min}=T^{best}-1$" and "$T^{max}=T^{best}+1$". On the other hand, the user may be asked to input the lower limit value $T^{min}$ and the upper limit value $T^{max}$, and the remaining one value may be taken as the average value, that is, "$T^{best}=(T^{min}+T^{max})/2$". In doing so, it is possible to calculate the air conditioning temperature setting value at which the user can obtain the awakening effect within a thermally comfortable range.

Similarly, the lower limit value $L^{min}$, the upper limit value $L^{max}$, and the comfort value $L^{best}$ of the lighting output setting value may be set by the user by providing an input interface. The user may be asked to input each of the three values. The user may be asked to input the comfort value $L^{best}$ only, and the remaining two values may be set to a value 20% lower or higher than that does not impair comfort, that is, "$L^{min}=L^{best}-20$" and "$L^{max}=L^{best}+20$". Here, the unit of $L^{min}$, $L^{max}$, and $L^{best}$ are percentages. For example, the value of $L^{min}$ may be 0% and the value of $L^{max}$ may be 100%.

On the other hand, the user may be asked to input the lower limit value $L^{min}$ and the upper limit value $L^{max}$, and the remaining one value may be taken as the average value, that is, "$L^{best}=(L^{min}+L^{max})/2$". In doing so, it is possible to calculate the lighting output setting value at which the user can obtain the awakening effect within a comfortable range of brightness.

The penalty coefficient $p_T$ of the air conditioning temperature is preferably "$p_T=1/1[point/° C.]$" because the temperature 1° C. lower or higher than the comfort value $T^{best}$ is the reference of discomfort.

The penalty coefficient $p_T$ of the lighting output is preferably "$p_L=1/20[point/\%]$" because 20% lower or higher than the comfort value $T^{best}[L^{best}]$ is the reference of discomfort.

The upper limit value $p^{max}$ of the penalty score is preferably 1 or more and less than 2. For example, "$p^{max}=1.5$" is preferable. This is because it is empirically known that tolerance for discomfort caused by a plurality of environment control devices at the same time is at most about two types.

Here, the arousal level estimated value $a_i(\tau)$ in the index set N of the subject and at the relative time $\tau$ is a constant determined by information acquired from the second acquisition unit. Therefore, from the above, it can be seen that no special adjustment is required for all the constants and coefficients involved in the calculation of device setting values.

Figure 5:
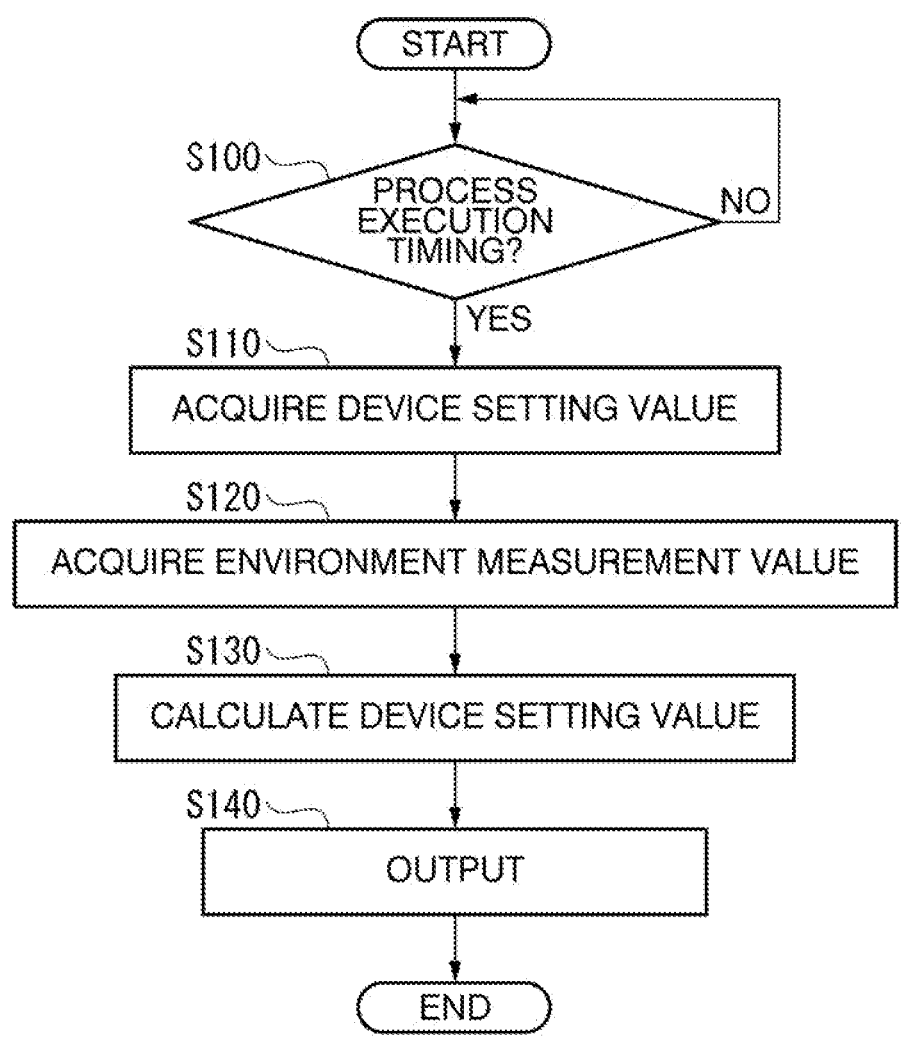
FIG. 5 is a flowchart showing a first example of a processing procedure in which the setting value calculation unit according to the example embodiment calculates a device setting value and sets it in an environment control device.
Figure 6:
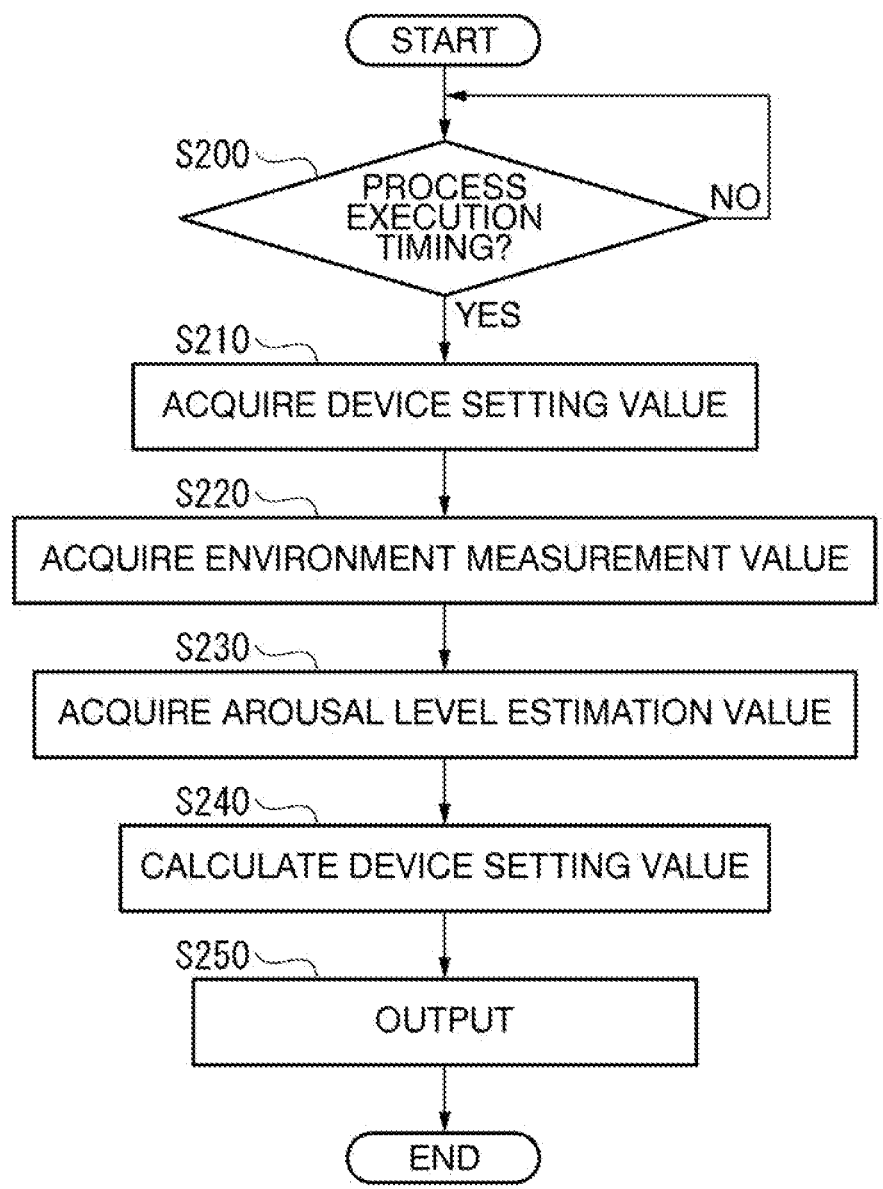
FIG. 6 is a flowchart showing a second example of the processing procedure in which the setting value calculation unit according to the example embodiment calculates a device setting value and sets it in the environment control device.

The setting value calculation unit 184 executes calculation through the procedure shown in FIG. 5 or FIG. 6. It is preferable that the calculation be executed at constant intervals of $\Delta\tau$.

FIG. 5 is a flowchart showing a first example of a processing procedure in which the setting value calculation unit 184 calculates a device setting value and sets it in the environment control device 200. FIG. 5 shows an example of a case in which the setting value calculation unit 184 calculates a device setting value without using an arousal level estimated value.

In the process of FIG. 5, the setting value calculation unit 184 determines whether or not the execution timing of the process for calculating a device setting value has arrived (Step S100). If the execution timing is determined as having not arrived (Step S100: No), the process returns to Step S100. As a result, the setting value calculation unit 184 waits for the execution timing of the process for calculating a device setting value to arrive.

On the other hand, if the execution timing of the process for calculating a device setting value is determined as having arrived (Step S100: Yes), the setting value calculation unit 184 acquires a device setting value from the monitoring control unit 181 (Step S110).

The setting value calculation unit 184 acquires an environment measurement value (measurement value of the physical quantity measured by the environment measurement device 300) from the first acquisition unit 182 (Step S120). Then, the setting value calculation unit 184 solves the optimization problem as described above to calculate a device setting value (value for updating device setting value) (Step S130). In Step S130, the setting value calculation unit 184 calculates the device setting value without using an arousal level estimated value.

The setting value calculation unit 184 outputs the obtained device setting value to the monitoring control unit 181 (Step S140). The monitoring control unit 181 transmits the device setting value obtained from the setting value calculation unit 184 to the environment control device 200 via the communication unit 110, to thereby set the device setting value in the environment control device 200.

After Step S140, the setting value calculation unit 184 ends the process of FIG. 5.

FIG. 6 is a flowchart showing a second example of a processing procedure in which the setting value calculation unit 184 calculates a device setting value and sets it in the environment control device 200. FIG. 6 shows an example of a case in which the setting value calculation unit 184 calculates a device setting value, using an arousal level estimated value.

Step S200 to Step S220 of FIG. 6 are similar to Step S100 to Step S120 of FIG. 5.

After Step S220, the setting value calculation unit 184 acquires an arousal level estimated value from the second acquisition unit 183 (Step S230).

Then, the setting value calculation unit 184 solves the optimization problem as described above to calculate a device setting value (value for updating device setting value) (Step S240). In Step S240, the setting value calculation unit 184 calculates the device setting value, using the arousal level estimated value.

Step S250 is similar to Step S140 of FIG. 5.

After Step S250, the setting value calculation unit 184 ends the process of FIG. 6.

Figure 7:
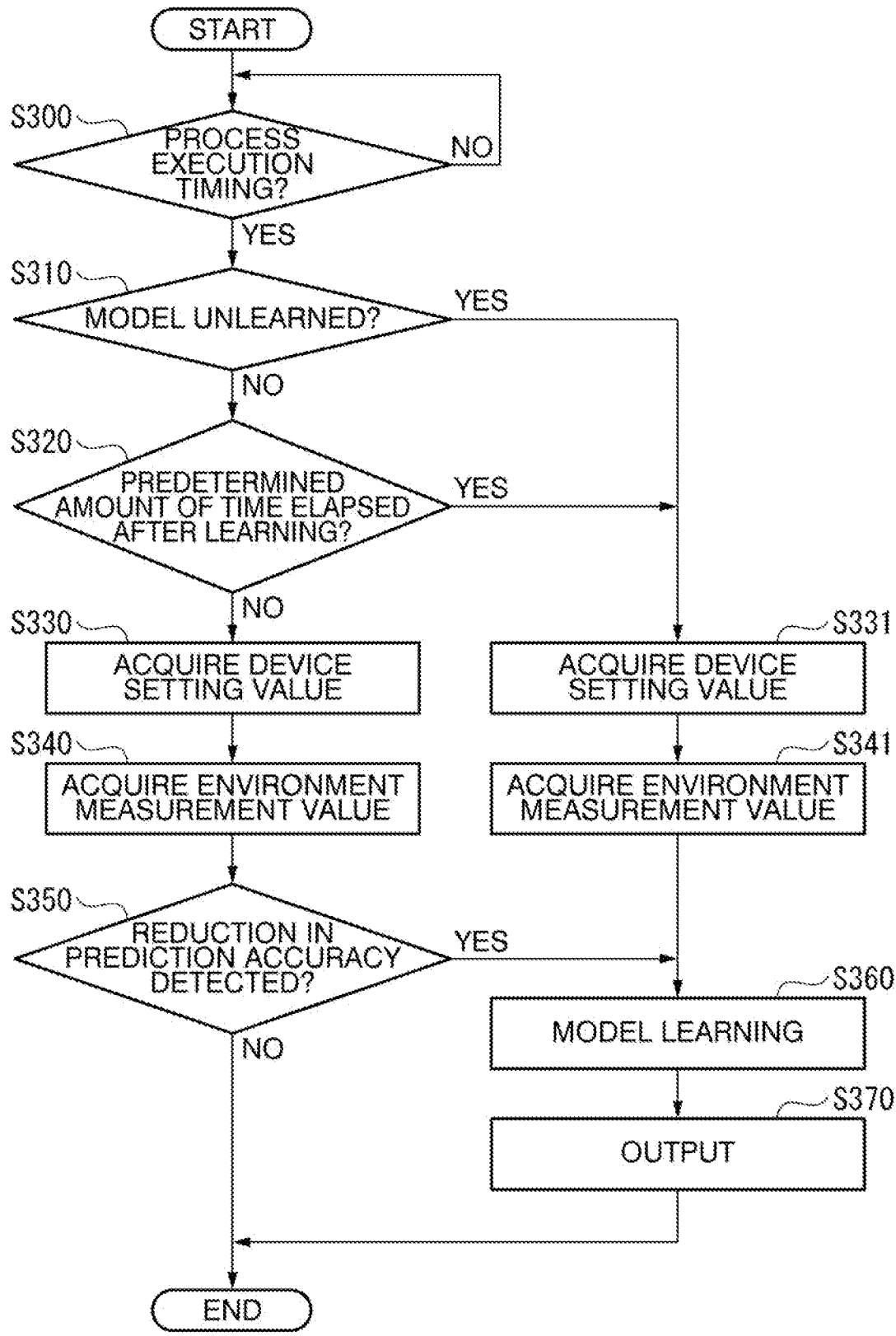
FIG. 7 is a flowchart showing an example of a processing procedure in which a physical quantity prediction model learning unit according to the example embodiment calculates a parameter value of a physical quantity prediction model by machine learning.

The physical quantity prediction model learning unit 188 executes calculation through the procedure shown in FIG. 7. For example, the calculation is executed at constant intervals within a range from 1 day to 2 weeks, and 1 day is preferable.

FIG. 7 is a flowchart showing an example of a processing procedure in which the physical quantity prediction model learning unit 188 calculates a parameter value of the physical quantity prediction model 171 by machine learning.

In the process of FIG. 7, the physical quantity prediction model learning unit 188 determines whether or not the execution timing of the process for calculating a parameter value has arrived (Step S300). If the execution timing is determined as having not arrived (Step S300: No), the process returns to Step S300. As a result, the physical quantity prediction model learning unit 188 waits for the execution timing of the process for calculating a parameter value to arrive.

On the other hand, if the execution timing of the process for calculating a parameter value is determined as having arrived (Step S300: Yes), the physical quantity prediction model learning unit 188 determines whether or not the physical quantity prediction model 171 is unlearned (Step S310).

Specifically, the physical quantity prediction model learning unit 188 attempts to acquire the parameter of the physical quantity prediction model 171 from the setting value calculation unit 184. If acquisition of the parameter is successful, the physical quantity prediction model learning unit 188 determines the physical quantity prediction model 171 as having been learned. On the other hand, if acquisition of the parameter is unsuccessful, the physical quantity prediction model learning unit 188 determines the physical quantity prediction model 171 as being unlearned.

If the physical quantity prediction model 171 is determined as having been learned (Step S310: No), the physical quantity prediction model learning unit 188 determines whether a predetermined amount of time has elapsed after the learning (Step S320). Specifically, the physical quantity prediction model learning unit 188 acquires the last update date and time of the parameter of the physical quantity prediction model 171 and compares the last update date and time with the current time to determine whether the difference therebetween exceeds a predetermined amount of time. In this case, the predetermined amount of time is, for example, an amount of time within the range of 1 day to 2 weeks, and 1 week is preferable.

If it is determined that the predetermined amount of time has not elapsed after learning (Step S320: No), the physical quantity prediction model learning unit 188 acquires a device setting value from the monitoring control unit 181 (Step S330). Moreover, the physical quantity prediction model learning unit 188 acquires a measurement value of a physical quantity (environment measurement value) from the first acquisition unit 182 (Step S340).

Then, the physical quantity prediction model learning unit 188 evaluates the prediction accuracy of the physical quantity prediction model 171, using the acquired data and the parameter value set in the physical quantity prediction model 171, and determines whether the prediction accuracy of the physical quantity prediction model 171 has decreased (Step S350).

For example, the physical quantity prediction model learning unit 188 determines whether or not the evaluation index is lower than a predetermined value where the evaluation index of the prediction accuracy is a mean absolute error rate, a correlation coefficient, or the like. When performing the determination, a plurality of evaluation indexes may be used. For example, the physical quantity prediction model learning unit 188 may use a mean absolute error rate and a correlation coefficient, and may determine the prediction accuracy as having decreased when the two evaluation indexes are both lower than predetermined values.

If it is determined that the prediction accuracy of the physical quantity prediction model 171 has not decreased (Step S350: No), the physical quantity prediction model learning unit 188 ends the process of FIG. 7.

On the other hand, if it is determined that the prediction accuracy of the physical quantity prediction model 171 has decreased (Step S350: Yes), the physical quantity prediction model learning unit 188 executes calculation of a model parameter value by means of machine learning, using the acquired device setting value and the measurement value of the physical quantity as learning data (Step S360). The physical quantity prediction model learning unit 188 may execute machine learning or the like by means of an appropriate method according to the functional form of the physical quantity prediction model. For example, in the case of a linear regression model, the physical quantity prediction model learning unit 188 executes support vector regression.

The physical quantity prediction model learning unit 188 updates the parameter value of the physical quantity prediction model 171 by outputting the obtained parameter value to the setting value calculation unit 184 (Step S370).

In the case where the physical quantity prediction model learning unit 188 evaluates the prediction accuracy using the parameter obtained by machine learning or the like and the prediction accuracy has improved compared to that in the pre-learning state, the physical quantity prediction model learning unit 188 may output the parameter and the date and time of learning calculation to the setting value calculation unit 184. The evaluation index of the prediction accuracy may be a mean absolute error rate, a correlation coefficient, or the like.

After Step S370, the physical quantity prediction model learning unit 188 ends the process of FIG. 7.

On the other hand, in Step S310, if the physical quantity prediction model 171 is determined as being unlearned (Step S310: Yes), the physical quantity prediction model learning unit 188 acquires a device setting value from the monitoring control unit 181 (Step S331). Moreover, the physical quantity prediction model learning unit 188 acquires a measurement value of a physical quantity (environment measurement value) from the first acquisition unit 182 (Step S341).

After Step S341, the process proceeds to Step S360.

On the other hand, if it is determined that a predetermined amount of time has elapsed after the learning (Step S320: Yes), the process proceeds to Step S331.

Figure 8:
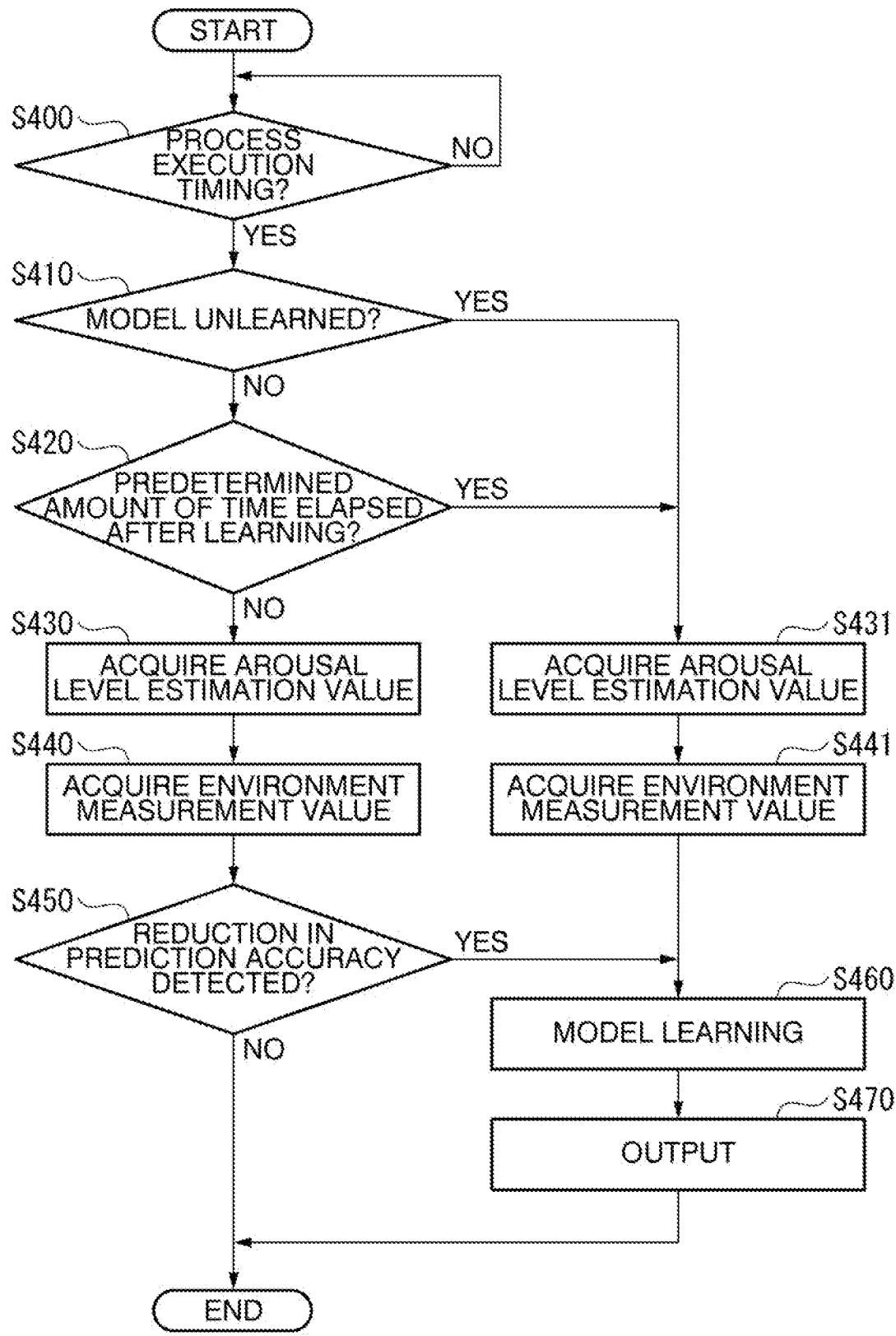
FIG. 8 is a flowchart showing an example of a processing procedure in which an arousal level prediction model learning unit according to the example embodiment calculates a parameter value of an arousal level prediction model by machine learning.

The arousal level prediction model learning unit 189 executes calculation through the procedure shown in FIG. 8. For example, the calculation is executed at constant intervals within a range from 1 week to 1 month. The preferred cycle is 1 month.

FIG. 8 is a flowchart showing an example of a processing procedure in which the arousal level prediction model learning unit 189 calculates a parameter value of the arousal level prediction model 172 by machine learning.

In the process of FIG. 8, the arousal level prediction model learning unit 189 determines whether or not the execution timing of the process for calculating a parameter value has arrived (Step S400). If the execution timing is determined as having not arrived (Step S400: No), the process returns to Step S400. As a result, the arousal level prediction model learning unit 189 waits for the execution timing of the process for calculating a parameter value to arrive.

On the other hand, if the execution timing of the process for calculating a parameter value is determined as having arrived (Step S400: Yes), the arousal level prediction model learning unit 189 determines whether or not the arousal level prediction model 172 is unlearned (Step S410).

Specifically, the arousal level prediction model learning unit 189 attempts to acquire the parameter of the arousal level prediction model 172 from the setting value calculation unit 184. If acquisition of the parameter is successful, the arousal level prediction model learning unit 189 determines the arousal level prediction model 172 as having been learned. On the other hand, if acquisition of the parameter is unsuccessful, the arousal level prediction model learning unit 189 determines the arousal level prediction model 172 as being unlearned.

If the arousal level prediction model 172 is determined as having been learned (Step S410: No), the arousal level prediction model learning unit 189 determines whether a predetermined amount of time has elapsed after the learning (Step S420). Specifically, the arousal level prediction model learning unit 189 acquires the last update date and time of the parameter of the arousal level prediction model 172 and compares the last update date and time with the current time to determine whether the difference therebetween exceeds a predetermined amount of time. This predetermined amount of time is, for example, an amount of time within the range of 2 weeks to 6 months, and 2 months is preferable.

If it is determined that the predetermined amount of time has not elapsed after learning (Step S420: No), the arousal level prediction model learning unit 189 acquires an arousal level estimated value from the second acquisition unit 183 (Step S430). Moreover, the arousal level prediction model learning unit 189 acquires a measurement value of a physical quantity (environment measurement value) from the first acquisition unit 182 (Step S440).

Then, the arousal level prediction model learning unit 189 evaluates the prediction accuracy of the arousal level prediction model 172, using the acquired data and the parameter value set in the arousal level prediction model 172, and determines whether the prediction accuracy of the arousal level prediction model 172 has decreased (Step S450).

For example, the arousal level prediction model learning unit 189 determines whether or not the evaluation index is lower than a predetermined value where the evaluation index of the prediction accuracy is a mean absolute error rate, a correlation coefficient, or the like. When performing the determination, a plurality of evaluation indexes may be used. For example, the arousal level prediction model learning unit 189 may use a mean absolute error rate and a correlation coefficient, and may determine the prediction accuracy as having decreased when the two evaluation indexes are both lower than predetermined values.

If it is determined that the prediction accuracy of the arousal level prediction model 172 has not decreased (Step S450: No), the arousal level prediction model learning unit 189 ends the process of FIG. 8.

On the other hand, if it is determined that the prediction accuracy of the arousal level prediction model 172 has decreased (Step S450: Yes), the arousal level prediction model learning unit 189 executes calculation of a model parameter value by means of machine learning, using the acquired arousal level estimated value and the measurement value of the physical quantity (environment measurement value) as learning data (Step S460). The arousal level prediction model learning unit 189 may execute machine learning by means of an appropriate method according to the functional form of the physical quantity prediction model. For example, in the case of a linear regression model, the arousal level prediction model learning unit 189 executes support vector regression.

The arousal level prediction model learning unit 189 updates the parameter value of the arousal level prediction model 172 by outputting the obtained parameter value to the setting value calculation unit 184 (Step S470).

In the case where the arousal level prediction model learning unit 189 evaluates the prediction accuracy using the parameter obtained by machine learning or the like and the prediction accuracy has improved compared to that in the pre-learning state, the arousal level prediction model learning unit 188 may output the parameter and the date and time of learning calculation to the setting value calculation unit 184. The evaluation index of the prediction accuracy may be a mean absolute error rate, a correlation coefficient, or the like.

After Step S470, the arousal level prediction model learning unit 189 ends the process of FIG. 8.

On the other hand, if the arousal level prediction model 172 is determined as being unlearned in Step S410 (Step S410: Yes), the arousal level prediction model learning unit 189 acquires an arousal level estimated value from the second acquisition unit 183 (Step S431). Moreover, the arousal level prediction model learning unit 189 acquires a measurement value of a physical quantity (environment measurement value) from the first acquisition unit 182 (Step S441).

After Step S441, the process proceeds to Step S460.

On the other hand, if it is determined that a predetermined amount of time has elapsed after the learning (Step S420: Yes), the process proceeds to Step S431.

The setting value determination unit 187 performs processing through the procedures shown in FIG. 9 to FIG. 12. For example, the calculation is executed at constant intervals within a range from 1 day to 2 weeks. The preferred cycle is 1 day.

Figure 9:
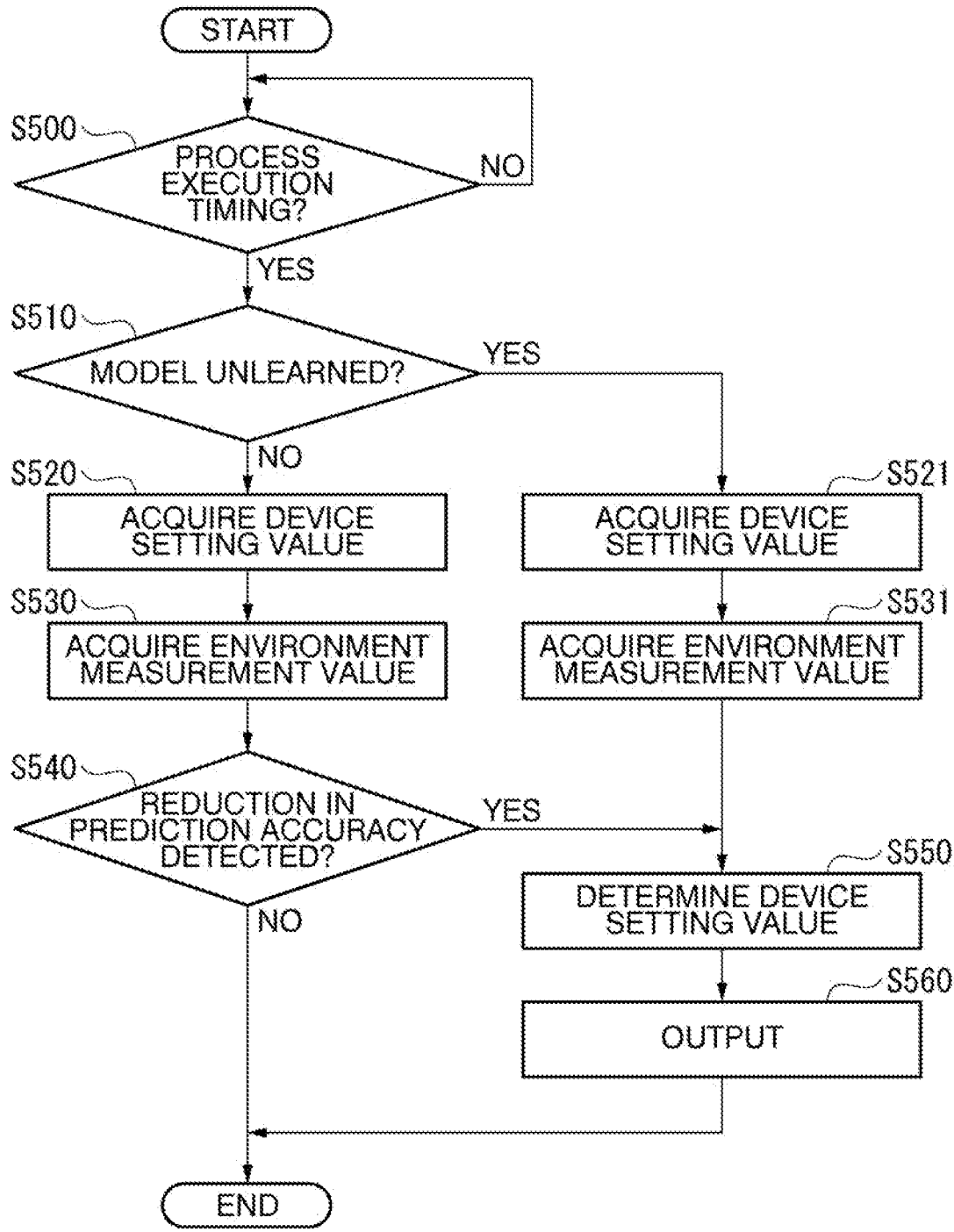
FIG. 9 is a diagram showing a first example of a processing procedure in which a setting value determination unit according to the example embodiment determines and outputs a device setting value.

FIG. 9 is a diagram showing a first example of a processing procedure in which the setting value determination unit 187 determines and outputs a device setting value. The setting value determination unit 187 performs the processing of FIG. 9 for each of the physical quantity prediction model 171 and the arousal level prediction model 172. For example, the setting value determination unit 187 applies the processing of FIG. 9 to each of the physical quantity prediction model 171 and the arousal level prediction model 172 while synchronizing therewith, and conditional branching may be performed while comprehensively taking into consideration the determination results of both models.

In the process of FIG. 9, the setting value determination unit 187 determines whether or not the execution timing of the process for determining a device setting value has arrived (Step S500). If the execution timing is determined as having not arrived (Step S500: No), the process returns to Step S500. As a result, the setting value determination unit 187 waits for the execution timing of the process for determining a device setting value to arrive.

On the other hand, if the execution timing of the process for determining a device setting value is determined as having arrived (Step S500: Yes), the setting value determination unit 187 determines whether one that is subject to a processing target of either the physical quantity prediction model 171 or the arousal level prediction model 172 is unlearned (Step S510).

Specifically, the setting value determination unit 187 attempts to acquire the parameter of one that is subject to the processing target of either the physical quantity prediction model 171 or the arousal level prediction model 172, from the setting value calculation unit 184. The setting value determination unit 187 determines the model, the parameter of which has been successfully acquired, as having been learned. On the other hand, the setting value determination unit 187 determines the model, the parameter of which has not been acquired, as being unlearned.

If the processing target model is determined as having been learned (Step S510: No), the setting value determination unit 187 acquires a device setting value from the monitoring control unit 181 (Step S520).

Moreover, if the processing target model is the physical quantity prediction model 171, the setting value determination unit 187 acquires a measurement value of a physical quantity (environment measurement value) from the first acquisition unit 182 (Step S530). If the processing target model is the arousal level prediction model 172, the setting value determination unit 187 acquires an arousal level estimated value from the second acquisition unit 183 in Step S530.

Then, the setting value determination unit 187 evaluates the prediction accuracy of the processing target model, using the acquired data and the parameter value of the processing target model, and determines whether the prediction accuracy thereof has decreased (Step S540).

For example, the setting value determination unit 187 determines whether or not the evaluation index is lower than a predetermined value where the evaluation index of the prediction accuracy is a mean absolute error rate or a correlation coefficient. When performing the determination, a plurality of evaluation indexes may be used. For example, the setting value determination unit 187 may use a mean absolute error rate and a correlation coefficient, and may determine the prediction accuracy as having decreased when the two evaluation indexes are both lower than predetermined values.

If it is determined that the prediction accuracy of the processing target model has not decreased (Step S540: No), the setting value determination unit 187 ends the process of FIG. 9.

On the other hand, if it is determined that the prediction accuracy of the processing target model has decreased (Step S540: Yes), the setting value determination unit 187 determines a device setting value (Step S550). Specifically, the setting value determination unit 187 determines a device set value that makes the variation as large as possible within the upper-lower limit range of the device setting value. The upper-lower limit ranges of device setting values are shown in Equations (4) and (5), for example. For example, the setting value determination unit 187 may periodically change the device setting value within the range between the upper limit value and the lower limit value as shown in FIG. 10.

Figure 10:
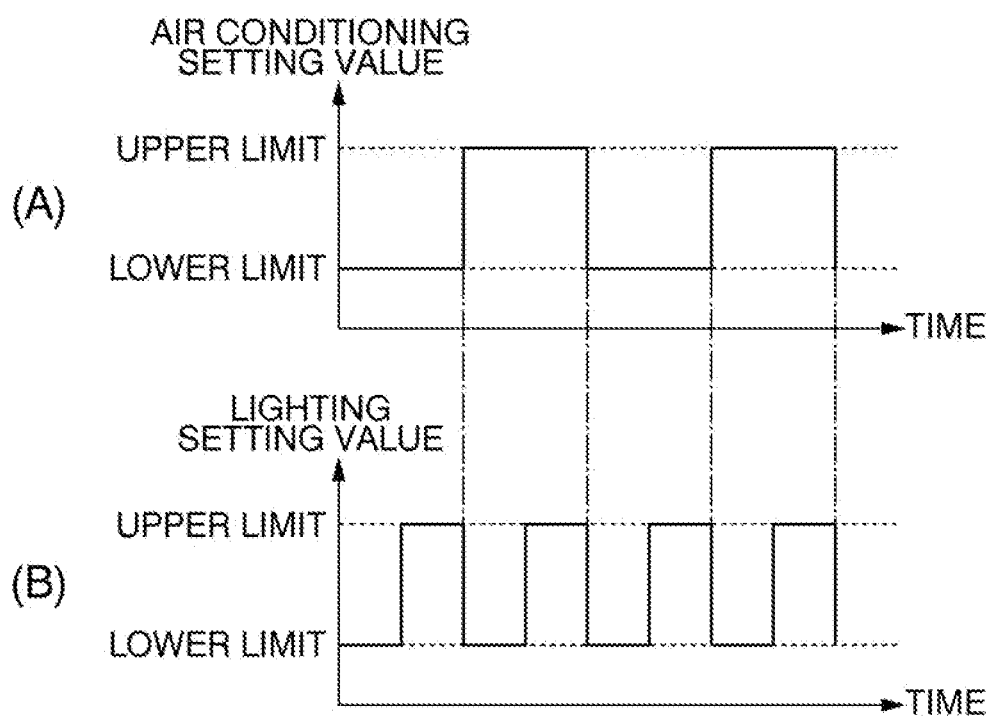
FIG. 10 is a diagram showing an example of the setting value determination unit setting device setting values for the environment control device according to the example embodiment.

FIG. 10 is a diagram showing an example of the setting value determination unit 187 setting device setting values for the environment control devices 200. The part (A) of FIG. 10 shows an example of the device setting value set by the setting value determination unit 187 when the environment control device 200 is an air conditioning device. The horizontal axis of the graph in the part (A) of FIG. 10 represents time. The vertical axis shows device setting values (air conditioning setting values (air conditioning temperature setting values)).

In the example of the part (A) of FIG. 10, the setting value determination unit 187 changes the air conditioning setting value significantly within the range between the upper limit value and the lower limit value. Specifically, the setting value determination unit 187 changes the air conditioning setting value to the upper limit value and to the lower limit value at constant intervals.

In this way, the setting value determination unit 187 significantly changes the device setting value for the environment control device 200 (air conditioning device in the example of FIG. 10), and it is thus possible to obtain data having comparatively large variations in the explanatory variable, which is suitable for machine learning or the like.

The part (B) of FIG. 10 shows an example of the device setting value set by the setting value determination unit 187 when the environment control device 200 is a lighting device. The horizontal axis of the graph in the part (B) of FIG. 10 represents time. The vertical axis represents device setting values (lighting setting values (lighting output setting values)).

In the example of the part (B) of FIG. 10, as with the case of the part (A) of FIG. 10, the setting value determination unit 187 changes the lighting setting value significantly within the range between the upper limit value and the lower limit value.

Comparing the example of the part (A) of FIG. 10 with the example of the part (B) of FIG. 10, the setting value determination unit 187 changes the device setting values in different cycles between the air conditioning device and the lighting device. Specifically, the setting value determination unit 187 changes the device setting value of the lighting device in half the cycle of the case of the air conditioning device.

In this way, when a plurality of types of environment control devices 200 are present, the setting value determination unit 187 changes device setting values so that the cycles thereof differ from each other and the combinations of the upper limit value and the lower limit value of the device setting values of the plurality of types of environment control devices 200 are comprehensive. At this time, since the change in temperature over time is slower than the change in illuminance over time, it is preferable that the cycle of fluctuation in the device setting value of the air conditioning device be longer than the cycle of fluctuation in the device setting value of the lighting device. In addition, the setting value determination unit 187 may determine the device setting value so as to follow a predetermined fluctuation pattern, or may simply randomly determine the device setting value.

When the device setting value is calculated (Step S550 in the example of FIG. 9), the setting value determination unit 187 transmits, to the setting value calculation unit 184, information not permitting execution of setting value calculation. The information not permitting execution is assigned with a validated date, and the setting value calculation unit 184 that has acquired the information not permitting execution does not execute the series of processes (Steps S110 to S140 or S210 to S240) until the validated date has been reached. For example, in Step S100 or Step S200, the process branches to "No".

After Step S550, the setting value determination unit 187 outputs the determined device setting value to the setting value calculation unit 184 to thereby set or update the parameter value of the processing target model (Step S560).

After Step S560, the setting value determination unit 187 ends the process of FIG. 9.

On the other hand, if the processing target model is determined in Step S510 as being unlearned (Step S510: Yes), the setting value determination unit 187 acquires a device setting value from the monitoring control unit 181 (Step S521).

Moreover, if the processing target model is the physical quantity prediction model 171, the setting value determination unit 187 acquires a measurement value of a physical quantity from the first acquisition unit 182 (Step S531). If the processing target model is the arousal level prediction model 172, the setting value determination unit 187 acquires an arousal level estimated value from the second acquisition unit 183 in Step S531.

After Step S531, the process proceeds to Step S550.

Figure 11:
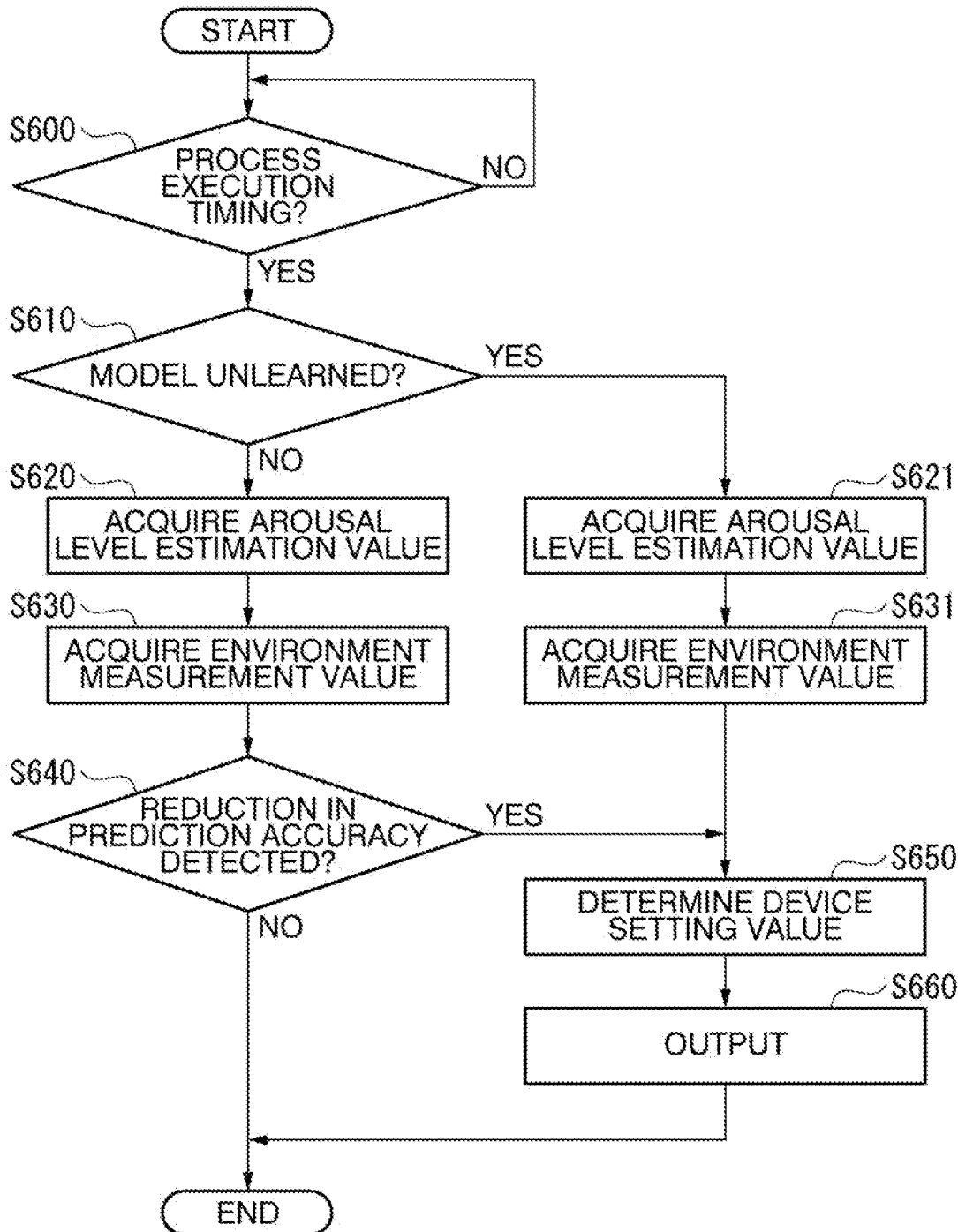
FIG. 11 is a diagram showing a second example of the processing procedure in which the setting value determination unit according to the example embodiment determines and outputs a device setting value.

FIG. 11 is a diagram showing a second example of the processing procedure in which the setting value determination unit 187 determines and outputs a device setting value. While FIG. 9 shows an example of the case where the processing target model is the physical quantity prediction model 171, FIG. 11 shows an example of the case where the processing target model is the arousal level prediction model 172. Therefore, the setting value determination unit 187 acquires a device setting value in both Step S520 and Step S521 of FIG. 9, whereas the setting value determination unit 187 acquires an arousal level estimated value in both Step S620 and Step S621 of FIG. 11.

In other respects, the processing of FIG. 11 is similar to that in the case of FIG. 9.

As described above, when a device setting value is calculated, the setting value determination unit 187 transmits, to the setting value calculation unit 184, information not permitting execution of setting value calculation. In FIG. 11, the setting value determination unit 187 transmits to the setting value calculation unit 184 information not permitting execution of setting value calculation in Step S650.

Figure 12:
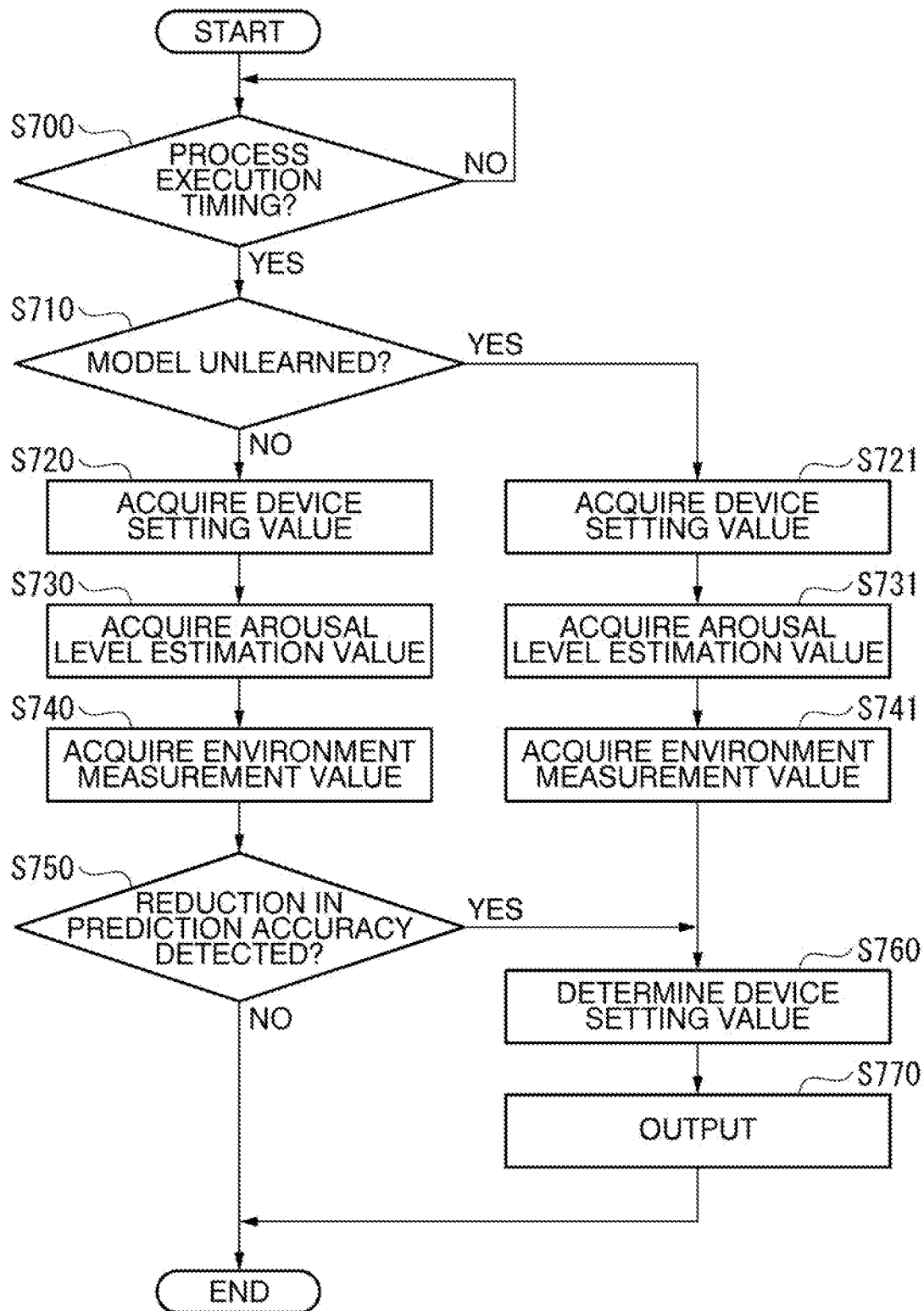
FIG. 12 is a diagram showing a third example of the processing procedure in which the setting value determination unit according to the example embodiment determines and outputs a device setting value.

FIG. 12 is a diagram showing a third example of the processing procedure in which the setting value determination unit 187 determines and outputs a device setting value. FIG. 9 shows an example of the case where the processing target model is the physical quantity prediction model 171, and FIG. 11 shows an example of the case where the processing target model is the arousal level prediction model 172. In contrast, FIG. 12 shows an example of the case where the physical quantity prediction model 171 and the arousal level prediction model 172 are both processing targets.

Accordingly, the setting value determination unit 187 acquires a device setting value in the process of FIG. 9 and the setting value determination unit 187 acquires an arousal level estimated value in the process of FIG. 11, whereas the setting value determination unit 187 acquires both a device setting value and an arousal level estimated value in the process of FIG. 12. Specifically, the setting value determination unit 187 acquires a device setting value in Step S720 and Step S721 of FIG. 12, and acquires an arousal level setting value in Step S730 and Step S731.

If, in Step S710 of FIG. 12, at least either one of the physical quantity prediction model 171 and the arousal level prediction model 172 is determined as Yes, the process may branch to Yes. Also, regarding Step S750, if at least either one is determined as Yes, the process may branch to Yes. Also, regarding Step S700, if at least either one is determined as Yes, the process may branch to Yes. In this way, the processing of the physical quantity prediction model 171 and the processing of the arousal level prediction model 172 may be synchronized, and conditional branching may be performed in consideration of both models comprehensively.

Alternatively, in the case where the physical quantity prediction model 171 and the arousal level prediction model 172 have different branch destinations, the processing of FIG. 12 may be performed separately.

In other respects, the processing of FIG. 12 is similar to that in the case of FIG. 9 and that in the case of FIG. 11.

As described above, when a device setting value is calculated, the setting value determination unit 187 transmits, to the setting value calculation unit 184, information not permitting execution of setting value calculation. In FIG. 12, the setting value determination unit 187 transmits to the setting value calculation unit 184 information not permitting execution of setting value calculation in Step S760.

As described above, the physical quantity prediction model 171 calculates a predicted value of a physical quantity on the basis of a setting value of the physical quantity that affects the subject. The arousal level prediction model 172 calculates a predicted value of an arousal level on the basis of a predicted value of the physical quantity calculated by the physical quantity prediction model 171. The setting value calculation unit 184 uses the physical quantity prediction model 171 and the arousal level prediction model 172 to calculate a setting value (device setting value) for controlling the arousal level of the subject, under constraint conditions related to the physical quantity. The monitoring control unit 181 sets the calculated setting value in the environment control device 200.

In this way, the physical quantity prediction model 171 calculates the predicted value of the physical quantity, and the arousal level prediction model 172 predicts the arousal level using the predicted value of the physical quantity. As a result, the variation in physical quantity can be incorporated into the prediction of arousal level. According to the arousal level control apparatus 100, in this respect, when performing arousal level control, it is possible to more accurately grasp the influence of the action on the surrounding environment on arousal level.

Moreover, according to the arousal level control apparatus 100, it is possible to eliminate the need for special adjustment for all constants and coefficients related to the calculation of device setting values as described above.

Also, the setting value calculation unit 184 calculates setting values so that the arousal level becomes even higher.

According to the arousal level control apparatus 100, it is possible to improve the arousal level of the subject, and it is possible, for example, to improve the work efficiency when the subject is performing tasks.

Moreover, the physical quantity prediction model 171 is a mathematical model capable of calculating a predicted value of a physical quantity at a moment at which a predetermined amount of time has elapsed, on the basis of a measurement value of a physical quantity and a setting value of a control target device.

Since the physical quantity prediction model 171 is configured as a mathematical model, it is possible to give meaning to the equations and the like that constitute the physical quantity prediction model 171. By interpreting this meaning, the validity of the physical quantity prediction model 171 can be verified.

The arousal level prediction model 172 is a mathematical model capable of calculating, on the basis of the temporal average value and variation of the physical quantity, the predicted value of the variation in the arousal level of a user at a moment at which a predetermined amount of time has elapsed.

Since the arousal level prediction model 172 is configured as a mathematical model, it is possible to give meaning to the equations and the like that constitute the arousal level prediction model 172. By interpreting this meaning, the validity of the arousal level prediction model 172 can be verified.

Also, the setting value calculation unit 184 calculates setting values so that the value of the objective function becomes even higher in an arousal level optimization model, which is a mathematical model. Specifically, the setting value calculation unit 184 solves an optimization problem indicated by this arousal level optimization model. This arousal level optimization model includes, as constraint conditions, a first constraint condition that is a physical quantity prediction model, a second constraint condition that is an arousal level prediction model, and a third constraint condition that the setting value of the environment control device is within a predetermined range. Moreover, the objective function of this arousal level optimization model is a function that calculates the sum value or average value of predicted values of variation in arousal level for one or more subjects and in one or more time steps.

Since the setting value calculation unit 184 uses an arousal level optimization model, which is a mathematical model, it is possible to give meaning to the equations and the like that constitute the arousal level optimization model. By interpreting this meaning, the validity of the arousal level optimization model can be verified. By verifying the validity of the arousal level optimization model, the validity of the processing performed by the setting value calculation unit 184 can be verified.

Moreover, the setting value calculation unit 184 calculates the setting value so that the trimmed mean of the predicted values of the variation in arousal level becomes even greater for one or more subjects and in one or more time steps.

As a result of the setting value calculation unit 184 using the trimmed mean, for example, when there are persons having an extremely small or, in contrast, an extremely large variation in the arousal level with respect to the variation in physical quantity among subjects, these subjects will not be over-evaluated, and thus the overall optimization can be achieved.

Also, the setting value calculation unit 184 calculates a setting value that satisfies the constraint condition related to comfort scores calculated for setting values.

As a result, the setting value calculation unit 184 can calculate a setting value in consideration of not only arousal level but also comfort. In this respect, the arousal level control apparatus 100 can balance arousal level and comfort.

Moreover, the setting value calculation unit 184 calculates each of a plurality of types of setting values so that the sum of the comfort penalty scores calculated for each of the plurality of types of setting values falls within a predetermined range.

As a result, when a plurality of types of environment control devices 200 are present, the setting value calculation unit 184 can ensure comfort in the plurality of types of environment control devices 200 as a whole. According to the arousal level control apparatus 100, in this respect, comfort can be ensured, and the degree of freedom is greater in setting the setting values by comparison with the case where comfort is ensured by controlling only one type of environment control device 200.

Furthermore, the arousal level prediction model 172 calculates a predicted value of an arousal level on the basis of a variation in a physical quantity in addition to a predicted value of the physical quantity.

It is conceivable that arousal level responds sensitively to the magnitude of variation in physical quantities. With the arousal level prediction model 172 predicting arousal level on the basis of the magnitude of the physical quantity, highly accurate prediction of arousal level is expected to be possible.

Also, the arousal level prediction model 172 calculates the predicted value of arousal level at least on the basis of temporal variance in the arousal level.

In the case where the degree of variance in arousal level is large, it is conceivable that the subject is drowsy and the arousal level of the subject is relatively low. With the arousal level prediction model 172 predicting arousal level on the basis of temporal variance in arousal level, more accurate understanding of the current state of arousal level is expected to be possible and the accuracy of predicting arousal level is expected to improve.

Moreover, the physical quantity prediction model learning unit 188 performs machine learning or the like on the basis of the measurement value of a physical quantity and a setting value of the physical quantity, to acquire the setting parameter value of the physical quantity prediction model 171.

As a result, the physical quantity prediction model learning unit 188 can automatically acquire a setting parameter value of the physical quantity prediction model 171 and does not require the administrator of the arousal level control apparatus 100 to manually obtain the set parameter value. According to the arousal level control apparatus 100, it is possible, in this respect, to decrease the time and effort of setting the physical quantity prediction model 171.

Also, the physical quantity prediction model learning unit 188 performs machine learning or the like at least in any one of the cases: where the setting parameter value of the physical quantity prediction model 171 has not been set; where the accuracy of prediction by means of the physical quantity prediction model 171 has decreased below a predetermined condition; and where a predetermined amount of time or more has elapsed since setting the setting parameter value of the physical quantity prediction model 171.

As a result, the physical quantity prediction model learning unit 188 can perform machine learning or the like as required. Therefore, the processing load on the physical quantity prediction model learning unit 188 can be lightweight as compared with the case where, for example, machine learning or the like is constantly repeated.

Moreover, the arousal level prediction model learning unit 189 performs machine learning on the basis of the measurement value of a physical quantity and the arousal level, to acquire a setting parameter value of the arousal prediction model.

As a result, the arousal level prediction model learning unit 189 can automatically set the setting parameter value of the arousal level prediction model 172. Therefore, there is no need for the administrator of the arousal level control apparatus 100 or the like to manually obtain the set parameter value. According to the arousal level control apparatus 100, it is possible, in this respect, to decrease the time and effort of setting the arousal level prediction model 172.

Also, the arousal level prediction model learning unit 189 performs machine learning at least in any one of the cases: where the setting parameter value of the arousal level prediction model 172 has not been set; where the accuracy of prediction by means of the arousal level prediction model 172 has decreased below a predetermined condition; and where a predetermined amount of time or more has elapsed since setting the setting parameter value of the arousal level prediction model 172.

As a result, the arousal level prediction model learning unit 189 can perform machine learning or the like as required. Therefore, the processing load on the arousal level prediction model learning unit 189 can be lightened as compared with the case where, for example, machine learning or the like is constantly repeated.

Furthermore, the setting value determination unit 187 determines a setting value within a predetermined range of the set value. The monitoring control unit 181 sets the setting value determined by the setting value determination unit 187 in the environment control device 200 instead of the setting value calculated by the setting value calculation unit 184 at least in any one of the cases: where the setting parameter value of the physical quantity prediction model 171 has not been set; where the accuracy of prediction made by the physical quantity prediction model 171 has decreased below a predetermined condition; where a predetermined amount of time or more has elapsed since setting the setting parameter value of the physical quantity prediction model 171; where the setting parameter value of the arousal level prediction model 172 has not been set; where the accuracy of prediction made by the arousal level prediction model 172 has become lower than a predetermined condition; and where a predetermined amount of time or more has elapsed since setting the setting parameter value of the arousal level prediction model 172.

With the setting value determination unit 187 determining the setting value, a setting value other than the optimum solution in the arousal level control by the setting value calculation unit 184 can be set in the environment control device 200, and a wider range of learning data can be obtained. With at least either the physical quantity prediction model learning unit 188 or the arousal level prediction model learning unit 189 performing machine learning or the like using the learning data obtained on the basis of the setting value determined by the setting value determination unit 187, machine learning can be performed with higher accuracy, and in this respect, the accuracy of the models can be improved.

Next, the configuration of an example embodiment of the present invention will be described, with reference to FIG. 13.

Figure 13:
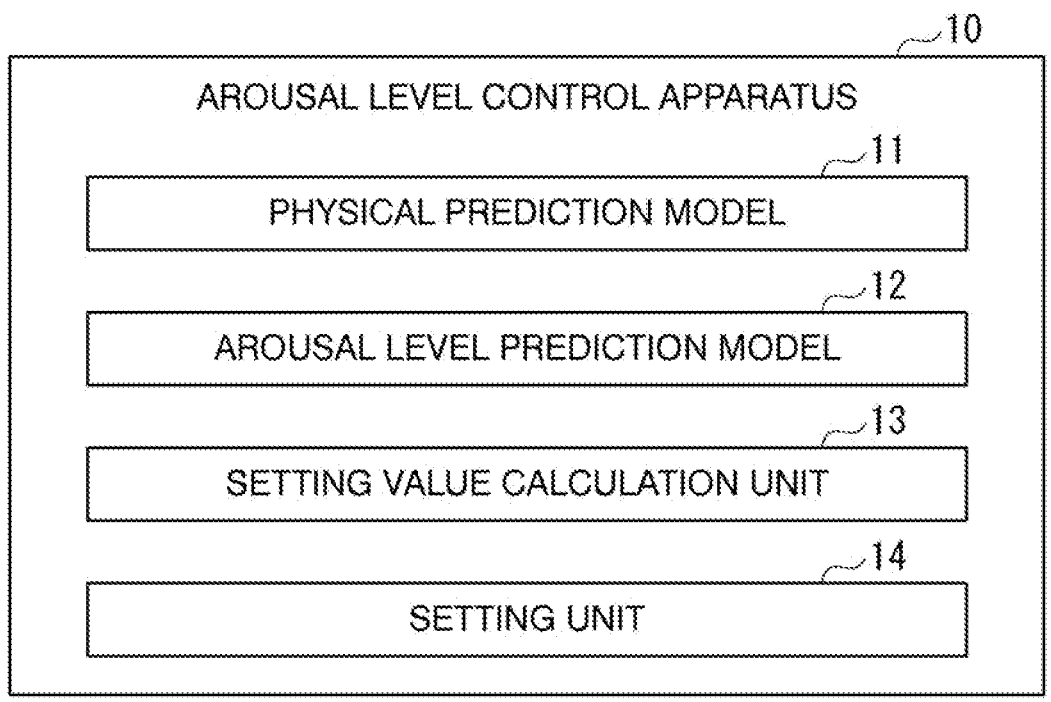
FIG. 13 is a diagram showing an example of a configuration of the arousal level control apparatus according to an example embodiment.

FIG. 13 is a diagram showing an example of a configuration of the arousal level control apparatus 10 according to an example embodiment. The arousal level control apparatus 10 shown in FIG. 13 includes a physical quantity prediction model (a storage unit that stores a physical quantity prediction model) 11, an arousal level prediction model (a storage unit that stores the arousal level prediction model) 12, a setting value calculation unit 13, and a setting unit 14.

In this configuration, the physical quantity prediction model 11 calculates a predicted value of a physical quantity on the basis of a setting value of the physical quantity that affects the arousal level of the subject. The arousal level prediction model 12 calculates a predicted value of the arousal level on the basis of the predicted value. The setting value calculation unit 13 calculates the setting value for controlling the arousal level of the subject, under constraint conditions related to the physical quantity by using the physical quantity prediction model and the arousal level prediction model. The setting unit 14 sets the calculated setting value in a control target device that affects the physical quantity.

In this way, the physical quantity prediction model 11 calculates the predicted value of the physical quantity and the arousal level prediction model 12 predicts the arousal level using the predicted value of the physical quantity. As a result, the variation in physical quantity can be incorporated into the prediction of arousal level. According to the arousal level control apparatus 10, in this respect, when performing arousal level control, it is possible to more accurately grasp the influence of the action on the surrounding environment on arousal level.

The configuration of the arousal level control apparatus 100 is not limited to a configuration using a computer. For example, the arousal level control apparatus 100 may be configured, using dedicated hardware such as an ASIC (Application Specific Integrated Circuit).

In the example embodiments of the present invention, arbitrary processes can also be realized by causing a CPU (Central Processing Unit) to execute a computer program.

In such a case, the program can be stored using various types of non-transitory computer readable media to be supplied to a computer. Non-transitory computer-readable media include various types of tangible storage media. Examples of non-temporary computer readable media include a magnetic recording medium (such as a flexible disk, a magnetic tape, or a hard disk drive), a magnetic optical recording medium (such as a magnetic optical disk), a CD-ROM (Read Only Memory), a CD-R, a CD-R/W, a DVD (Digital Versatile Disc), a BD (Blu-ray (registered trademark) Disc), and a semiconductor memory (such as a mask ROM, PROM (Programmable ROM), EPROM (Erasable PROM), flash ROM, or RAM (Random Access Memory)).

This application is based upon and claims the benefit of priority from Japanese patent application No. 2019-018212, filed Feb. 4, 2019, the disclosure of which is incorporated herein in its entirety by reference.

INDUSTRIAL APPLICABILITY

The present invention may be applied to an arousal level control apparatus, an arousal level control method, and a recording medium.

REFERENCE SYMBOLS

1 Arousal level control system
10, 100 Arousal level control apparatus
11, 171 Physical quantity prediction model
12, 172 Arousal level prediction model
13, 184 Setting value calculation unit (setting value calculation means)
14 Setting unit (setting means)
110 Communication unit (communication means)
170 Storage unit (storage means)
180 Control unit (control means)
181 Monitoring control unit (monitoring control means)
182 First acquisition unit (first acquisition means)
183 Second acquisition unit (second acquisition means)
185 Physical quantity prediction model computation unit (physical quantity prediction model computation means)
186 Arousal level prediction model computation unit (arousal level prediction model computation means)
187 Setting value determination unit (setting value determination means)
188 Physical quantity prediction model learning unit (physical quantity prediction model learning means)
189 Arousal level prediction model learning unit (arousal level prediction model learning means)
200 Environment control device
300 Environment measurement device
400 Arousal level estimation device

The invention claimed is:
1. An arousal level control apparatus comprising:
at least one memory configured to store instructions; and
at least one processor configured to execute the instructions to:
calculate a setting value of a control device under a constraint condition using an arousal level optimization model so that a value of an objective function is maximized; and
set the control device with the calculated setting value, wherein the control device is configured to affect a physical quantity of a surrounding environment that affects an arousal level of a subject, the arousal level optimization model includes the constraint condition and the objective function, the constraint condition includes a physical quantity prediction model, an arousal level prediction model, and a setting value range condition in which the setting value is within a predetermined range, the physical quantity prediction model is an explicit function that includes the physical quantity and the setting value as explanatory variables and has a predicted value of the physical quantity as an explained variable, the physical quantity prediction model is configured to be trained by machine learning, the arousal level prediction model is an explicit function that includes the physical quantity and variation thereof over time as explanatory variables and has a predicted value of variation of the arousal level over time as an explained variable, the arousal level prediction model is configured to be trained by machine learning, the objective function expresses a total value or an average value of a predicted value for one or more subjects including the subject, the predicted value for the one or more subjects is a predicted value of variation in an arousal level for the one or more subjects and two or more time steps that satisfy a predetermined condition, and the physical quantity includes a room temperature.

2. The arousal level control apparatus according to claim 1, wherein the subject includes a vehicle driver.

3. The arousal level control apparatus according to claim 1, wherein the constraint condition includes a comfort condition in which a sum of comfort penalty scores calculated for a plurality of setting values, including the setting value, is within a predetermined range.

4. The arousal level control apparatus according to claim 1, wherein the arousal level prediction model includes variation of the arousal level over time as an explanatory variable.

5. The arousal level control apparatus according to claim 1, wherein the arousal level prediction model includes temporal variance of the arousal level as an explanatory variable.

6. An arousal level control method executed by a computer, comprising:

calculating a setting value of a control device under a constraint condition using an arousal level optimization model so that a value of an objective function is maximized; and setting the control device with the calculated setting value, wherein the control device is configured to affect a physical quantity of a surrounding environment that affects arousal level of a subject, the arousal level optimization model includes the constraint condition and the objective function, the constraint condition includes a physical quantity prediction model, an arousal level prediction model, and a setting value range condition in which the setting value is within a predetermined range, the physical quantity prediction model is an explicit function that includes the physical quantity and the setting value as explanatory variables and has a predicted value of the physical quantity as an explained variable, the physical quantity prediction model is configured to be trained by machine learning, the arousal level prediction model is an explicit function that includes the physical quantity and variation thereof over time as explanatory variables and has a predicted value of variation of the arousal level over time as an explained variable, the arousal level prediction model is configured to be trained by machine learning, the objective function expresses a total value or an average value of a predicted value for one or more subjects including the subject, the predicted value for the one or more subjects is a predicted value of variation in an arousal level for the one or more subjects and two or more time steps that satisfy a predetermined condition, and the physical quantity includes a room temperature.

7. A non-transitory recording medium that stores a program causing a computer to execute:

calculating a setting value of a control device under a constraint condition using an arousal level optimization model so that a value of an objective function is maximized; and setting the control device with the calculated setting value, wherein the control device is configured to affect a physical quantity of a surrounding environment that affects arousal level of a subject, the arousal level optimization model includes the constraint condition and the objective function, the constraint condition includes a physical quantity prediction model, an arousal level prediction model, and a setting value range condition in which the setting value is within a predetermined range, the physical quantity prediction model is an explicit function that includes the physical quantity and the setting value as explanatory variables and has a predicted value of the physical quantity as an explained variable, the physical quantity prediction model is configured to be trained by machine learning, the arousal level prediction model is an explicit function that includes the physical quantity and variation thereof over time as explanatory variables and has a predicted value of variation of the arousal level over time as an explained variable, the arousal level prediction model is configured to be trained by machine learning, the objective function expresses a total value or an average value of a predicted value for one or more subjects including the subject, the predicted value for the one or more subjects is a predicted value of variation in an arousal level for the one or more subjects and two or more time steps that satisfy a predetermined condition, and the physical quantity includes a room temperature.

* * * * *